(12) United States Patent
Nelson et al.

(10) Patent No.: US 7,629,591 B2
(45) Date of Patent: Dec. 8, 2009

(54) SYSTEM AND METHOD FOR STRUCTURED ILLUMINATION AND COLLECTION FOR IMPROVED OPTICAL CONFOCALITY OF RAMAN FIBER ARRAY SPECTRAL TRANSLATOR IMAGING AND INTERACTIVE RAMAN PROBING

(75) Inventors: Matthew P. Nelson, Pittsburgh, PA (US); Patrick J. Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 266 days.

(21) Appl. No.: 11/712,917

(22) Filed: Mar. 2, 2007

(65) Prior Publication Data

US 2007/0205379 A1    Sep. 6, 2007

Related U.S. Application Data

(60) Provisional application No. 60/778,588, filed on Mar. 2, 2006.

(51) Int. Cl.
*G01N 21/64* (2006.01)
(52) U.S. Cl. .................................... 250/458.1
(58) Field of Classification Search ............... 250/458.1
See application file for complete search history.

(56) References Cited

U.S. PATENT DOCUMENTS

| | | | |
|---|---|---|---|
| 4,781,458 A | 11/1988 | Angel et al. | |
| 5,491,344 A * | 2/1996 | Kenny et al. | 250/461.1 |
| 5,534,997 A | 7/1996 | Schrader | |
| 5,615,673 A | 4/1997 | Berger et al. | |
| 5,963,319 A | 10/1999 | Jarvis et al. | |
| 6,100,975 A | 8/2000 | Smith et al. | |
| 6,483,581 B1 | 11/2002 | Ben-Amotz et al. | |
| 6,486,948 B1 | 11/2002 | Zeng | |
| 6,717,668 B2 * | 4/2004 | Treado et al. | 356/327 |
| 6,867,858 B2 | 3/2005 | Owen et al. | |
| 6,917,423 B2 * | 7/2005 | Gardner et al. | 356/301 |
| 7,072,770 B1 | 7/2006 | Schweitzer et al. | |
| 2002/0001089 A1 * | 1/2002 | Price | 356/601 |
| 2002/0048610 A1 | 4/2002 | Cima et al. | |
| 2003/0059837 A1 | 3/2003 | Levinson et al. | |
| 2003/0162226 A1 | 8/2003 | Cima et al. | |
| 2003/0227628 A1 * | 12/2003 | Kreimer et al. | 356/419 |
| 2005/0089923 A9 | 4/2005 | Levinson et al. | |

(Continued)

OTHER PUBLICATIONS

Manolakis, D. et al., "Hyperspectral Subpixel Target Detection Using the Linear Mixing Model," IEEE Trans. on Geoscience and Remote Sensing, Jul. 2001, V. 39, No. 7, p. 1392-1409.

(Continued)

*Primary Examiner*—David P Porta
*Assistant Examiner*—Marcus H Taningco
(74) *Attorney, Agent, or Firm*—Duane Morris LLP

(57) ABSTRACT

The disclosure relates generally to methods and apparatus for using a fiber array spectral translator-based ("FAST") spectroscopic system for improved imaging, spectral analysis, and interactive probing of a sample. In an embodiment, the confocality of a fiber array spectral translator-based spectroscopic system is improved through the use of structured illumination and/or structured collection of photons. User input may be received and acted upon to allow a user to interactively in real time and/or near real time view and analyze specific regions of the sample.

79 Claims, 18 Drawing Sheets

U.S. PATENT DOCUMENTS

2005/0095696 A9    5/2005    Lemmo et al.
2005/0119587 A1*  6/2005    Roessler et al. ............ 600/562
2005/0191614 A1    9/2005    Cima et al.

OTHER PUBLICATIONS

Anquetil, P., et al. "Laser Raman Spectroscopic Analysis of Polymorphic Forms in Microliter Fluid Volumes," J. of Pharma. Sciences, Jan. 2003, V. 92, No. 1, pp. 149-161.

Carter, J.C., et al., Multi-Wavelength Raman Imaging Using a Small-Diameter Image Guide with a Dimension-Reduction Imaging Array, Appl. Spectro, 2003, V57, No. 7, pp. 761-767.

Ma, Jiaying and Ben-Amotz, Dor, "Rapid Micro-Raman Imaging Using Fiber-Bundle Image Compression," Applied Spectroscopy; 1997, V. 51, No. 12, pp. 1845-1849.

Nelson, M. et al., Single-Frame Chemical Imaging: Dimens. Reduction Fiber-Optic Array Improvements & Appl. to Laser-Induced Breakdown Spectroscopy, 1999, V53, #7, pp. 751-759.

Nelson, M. et al. "Single-Shot Multiwavelength Imageing of Laser Plumes," Applied Spectroscopy, 1998, V. 52, No. 2, pp. 179-187.

* cited by examiner

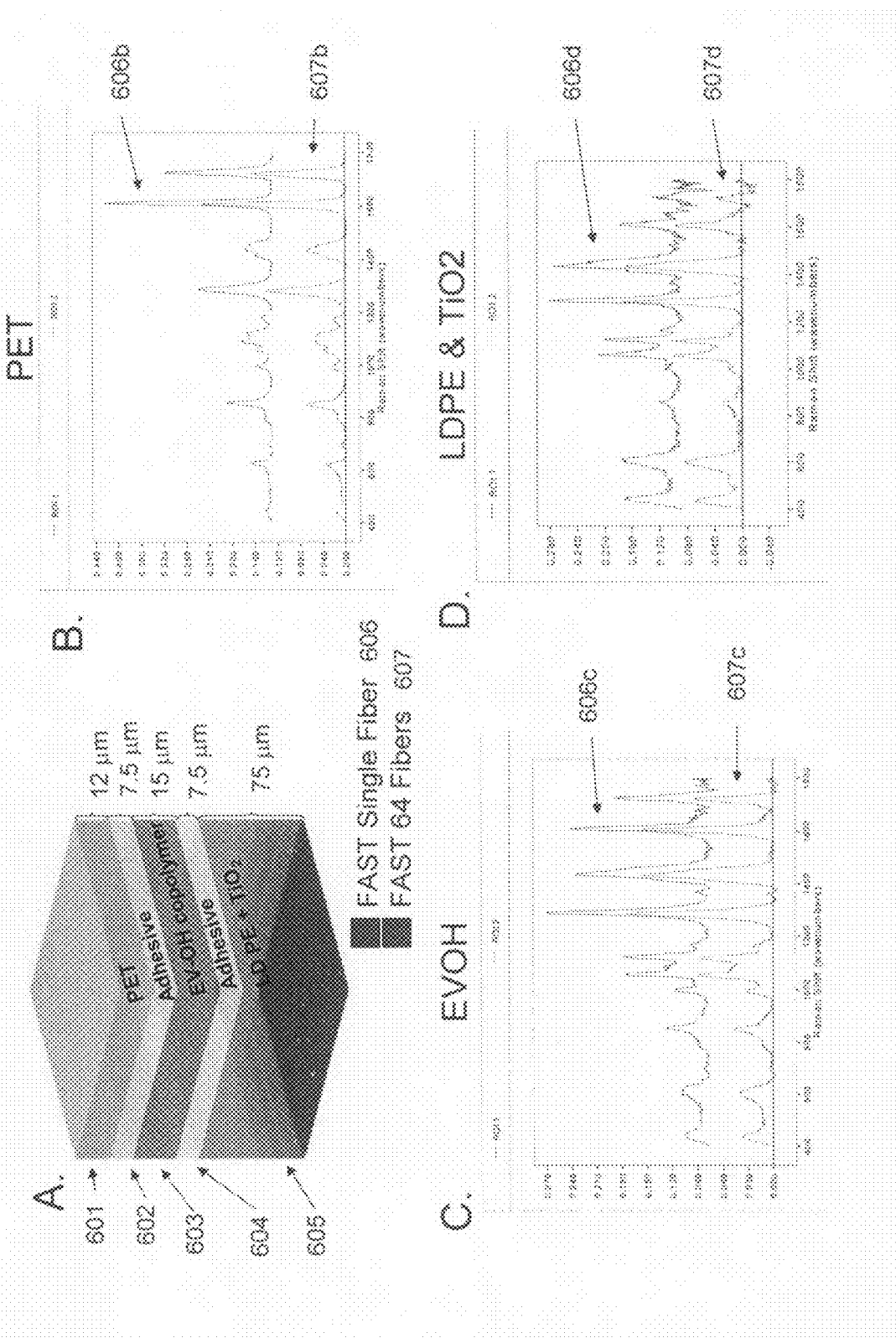

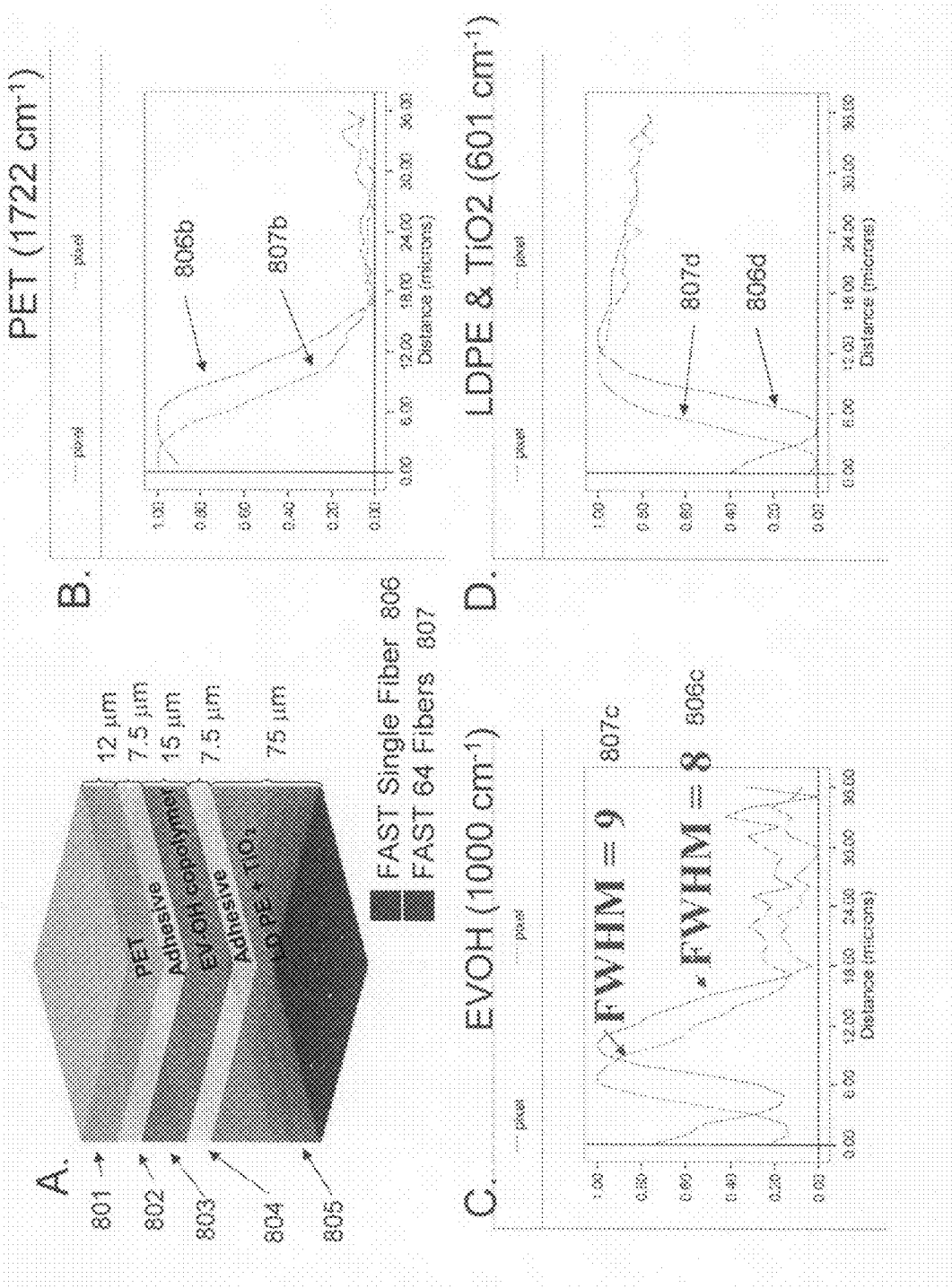

SYSTEM AND METHOD FOR STRUCTURED ILLUMINATION AND COLLECTION FOR IMPROVED OPTICAL CONFOCALITY OF RAMAN FIBER ARRAY SPECTRAL TRANSLATOR IMAGING AND INTERACTIVE RAMAN PROBING

PRIORITY INFORMATION

The instant disclosure claims the filing-date benefit of Provisional Application No. 60/778,588 filed 2 Mar. 2006, entitled "Spectral Unmixing in a Fiber Array Spectral Translator (FAST) Based Polymorph Screening", the disclosure of which is incorporated herein in its entirety. The instant disclosure is also related to U.S. patent application Ser. No. 10/812,233, filed 29 Mar. 2004, entitled "Method for Identifying Components of a Mixture via Spectral Analysis" and to U.S. patent application Ser. No. 11/000,683, filed 20 Nov. 2004, entitled "Multipoint Method for identifying Hazardous Agents", the disclosure of each is hereby incorporated by reference in its entirety. All of the foregoing are commonly assigned to the assignee of the instant disclosure.

BACKGROUND

A fiber array spectral translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector.

Given the advantageous ability of a FAST system to acquire hundreds to thousands of full spectral range, spatially-resolved spectra, such as Raman spectra, substantially simultaneously, a FAST system may be used in a variety of situations to help resolve difficult spectrographic problems such as the presence of polymorphs of a compound, sometimes referred to as spectral unmixing.

Chemical images may generally be acquired using one of two classes of approaches: (1) scanning, and (2) widefield chemical imaging. In scanning methods, a radiation source is focused onto the surface of a sample and a spectrum from each spatial position is collected using a dispersive spectrograph or interferometer. Long data collection times are common with scanning methods since the duration of the experiment is proportional to the number of image pixels. Because of such long data collection times, scanned images are captured at low image definition, which relates directly to the limited utility of the technique as an imaging tool for the routine assessment of material morphology. Furthermore, the spatial resolution of the image is limited by the size of the source illumination on the sample and the rastering mechanism, which requires the use of moving mechanical parts that are challenging to operate reproducibly. In addition, for light-absorbing materials, scanning methods present an enormous challenge. These materials have low damage thresholds, requiring the use of low laser power densities to minimize local thermal expansion and sample degradation.

Despite the limitations, scanning methods are relatively mature techniques and have been applied in a number of applications. An advantage of scanning-based chemical imaging is the ability to capture the entire spectrum in an efficient manner. This advantage is best realized in the research evaluation of new material systems where the underlying spectroscopy is not well understood, and therefore, benefits may be available from the analysis of the entire spectrum.

In widefield chemical imaging, the entire sample field of view is illuminated and analyzed simultaneously. Numerous widefield chemical imaging approaches have been demonstrated, with the majority of methods involving the recording of an image at discrete spectral intervals though an imaging spectrometer (i.e., LCTF (Liquid Crystal Tunable Filter), AOTF (Acousto-Optic Tunable Filter), etc.).

Because both (X-Y) spatial dimensions are collected simultaneously in widefield Chemical Imaging using imaging spectrometers, the experiment duration is proportional to the number of spectral channels and not to the number of image pixels. The widefield advantages are best realized when high fidelity images at a limited number of wavelengths provide sufficient chemical and spatial information. In most materials characterization applications, only a limited number of spectral bands (typically <100) are required to analyze the analytes of interest. By reducing the number of spectral channels, the duration of the widefield experiment decreases without losing spatial resolution. In addition, time-dependent changes in the sample are only observed in the spectral dimension, which simplifies the analysis of chemical images in widefield imaging.

Conversely, attempts to reduce the duration of scanning experiments (in the scanning approach discussed above) compromise either the spatial resolution or the field of view. Reducing the number of spectral channels in scanning mode has little effect on the experiment duration since the entire chemical spectrum is captured simultaneously (in the scanning approach discussed above). Scanning experiments record time dependent sample changes as spatial variations. Pixels collected at different times often have induced spectral differences that complicate analysis.

A limitation that widefield illumination methods suffer from is secondary scattering of illumination that fundamentally reduces the inherent confocality associated with the measurement(s). Secondary scattering occurs when illumination of a first location results in an emission or scattering of radiation that migrates to a second sample location and is detected as if it had originated in the second spatial location. On the other hand, the scanning approach discussed above is generally less susceptible to secondary illumination effects since the illumination is first restricted to a first sample location and the collected light is then restricted to the same sample location through use of pinhole apertures. Line scanning approaches are slightly more susceptible to secondary scattering effects along the sample axis that is aligned in parallel with the entrance slit of the spectrograph compared to point mapping/scanning approaches.

FAST enables full spectral acquisition for hundreds to thousands of spatially resolved spectra in a single image frame—dramatically increasing data acquisition rates compared to current tunable filter based technologies. Software is used to extract the spatial/spectral information to reconstruct hyperspectral (chemical imaging) data cubes of the original object. Furthermore, FAST is a rugged technology that operates over an extensive spectral range from ultraviolet (UV) to infrared (IR).

As with alternative widefield chemical imaging methods, FAST based systems are susceptible to secondary scattering of radiation. The present disclosure describes systems and methods for overcoming the limitations of the prior art including novel sample illumination and light collection systems and methods to enhance the confocality of FAST based spectroscopy systems.

Accordingly, it is on object of the present disclosure to provide an improved FAST system for detecting photons from a sample including increasing the confocality of the system by directing only photons in a predetermined group of plural fibers in the FAST system to a photon detector, wherein each fiber in the predetermined group is associated with a predetermined different portion of the sample wherein each of the predetermined different portions is smaller than an illuminated portion of the sample.

It is another object of the present disclosure to provide a system for detecting photons from a sample, comprising a photon source for illuminating a first portion of a sample with first photons to thereby produce second photons; a fiber array spectral translator comprising plural fibers for receiving the second photons and directing the second photons to the photon detector, wherein only a first predetermined group of the plural fibers receive and direct the second photons to the photon detector, and wherein each fiber in the first predetermined group is associated with a predetermined different second portion of the sample wherein each of the predetermined different second portions is smaller than the first portion; and the aforementioned photon detector for detecting the second photons. Furthermore, the system may further comprise a display device, and a microprocessor unit operatively connected to the photon detector and to the display device, wherein the photon detector sends to the microprocessor a first signal representative of the second photons, and wherein the microprocessor unit forms a second signal from the first signal and sends the second signal to the display device to display a first visual representation of the second signal.

It is a further object of the present disclosure to provide a method for detecting photons from a sample, comprising illuminating a first portion of a sample with first photons to thereby produce second photons; receiving the second photons using a fiber array spectral translator comprising plural fibers and directing the second photons to the photon detector using the fiber array spectral translator, wherein only a first predetermined group of the plural fibers receive and direct the second photons to the photon detector, and wherein each fiber in the first predetermined group is associated with a predetermined different second portion of the sample wherein each of the predetermined different second portions is smaller than said first portion; and detecting the second photons using the photon detector.

BRIEF DESCRIPTION OF THE DRAWINGS

FIGS. 6A through 6D illustrate a test sample (FIG. 6A) and graphs (FIGS. 6B-6D) showing data collected from the test sample using a FAST based spectroscopy system according to an embodiment of the disclosure.

FIGS. 8A through 8D illustrate a test sample (FIG. 8A) and graphs (FIGS. 8B-8D) showing data collected from the test sample using a FAST based spectroscopy system according to an embodiment of the disclosure.

DETAILED DESCRIPTION

Figure 1:
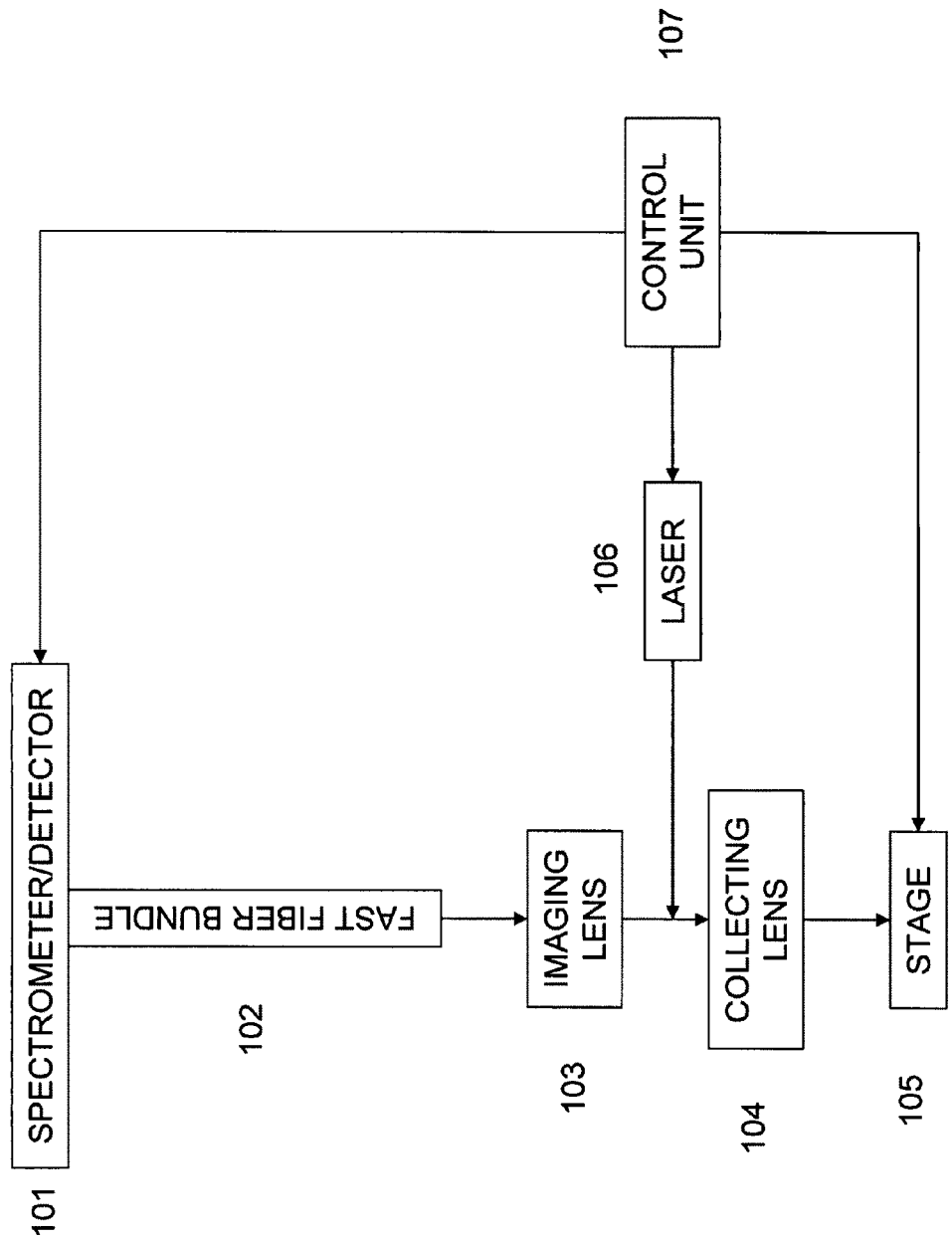
FIG. 1 is a schematic block diagram of a of a fiber array spectral translator ("FAST") based spectroscopy system.
Figure 2:
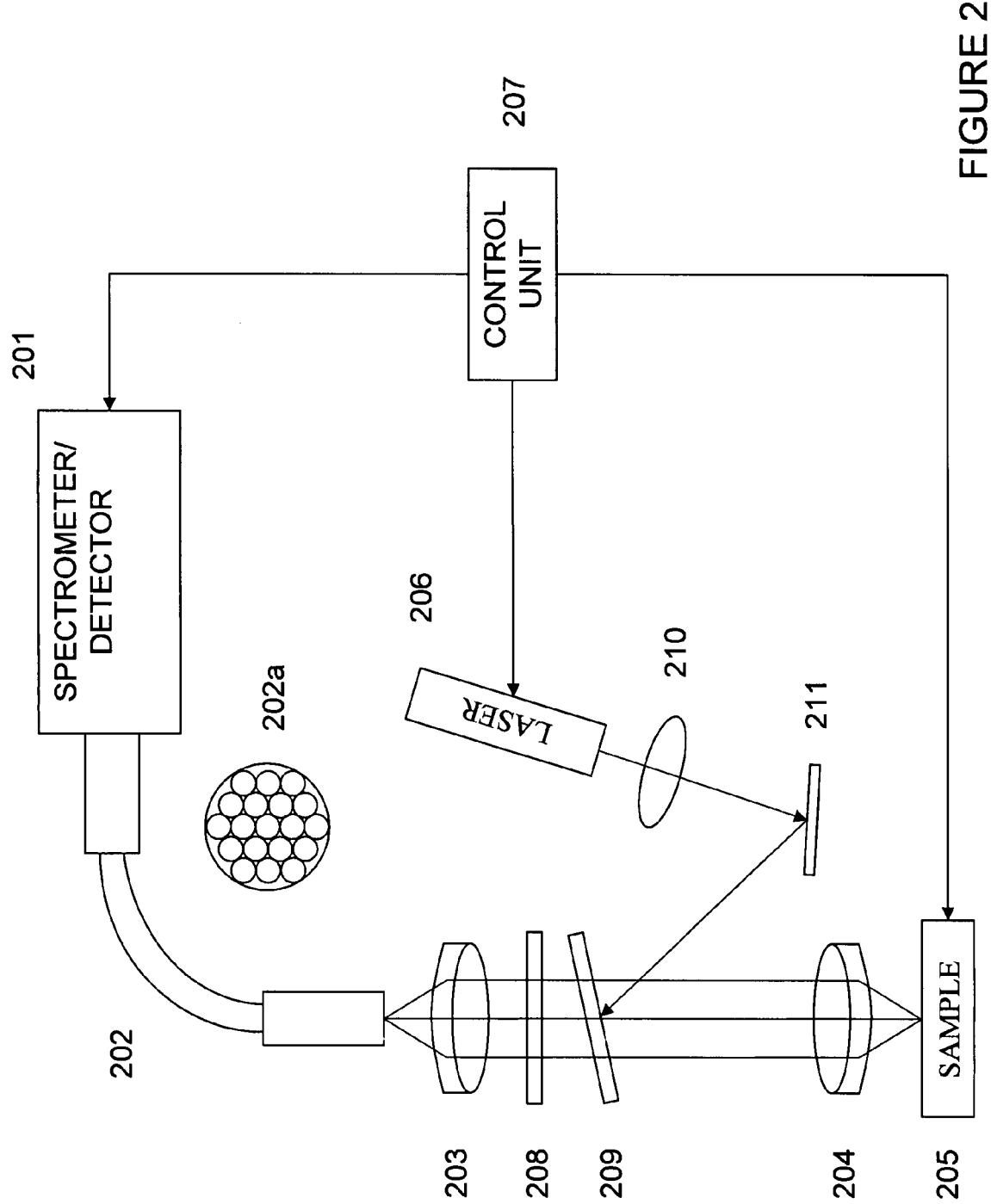
FIG. 2 is a is a schematic drawing of a FAST based spectroscopy system.
Figure 3:
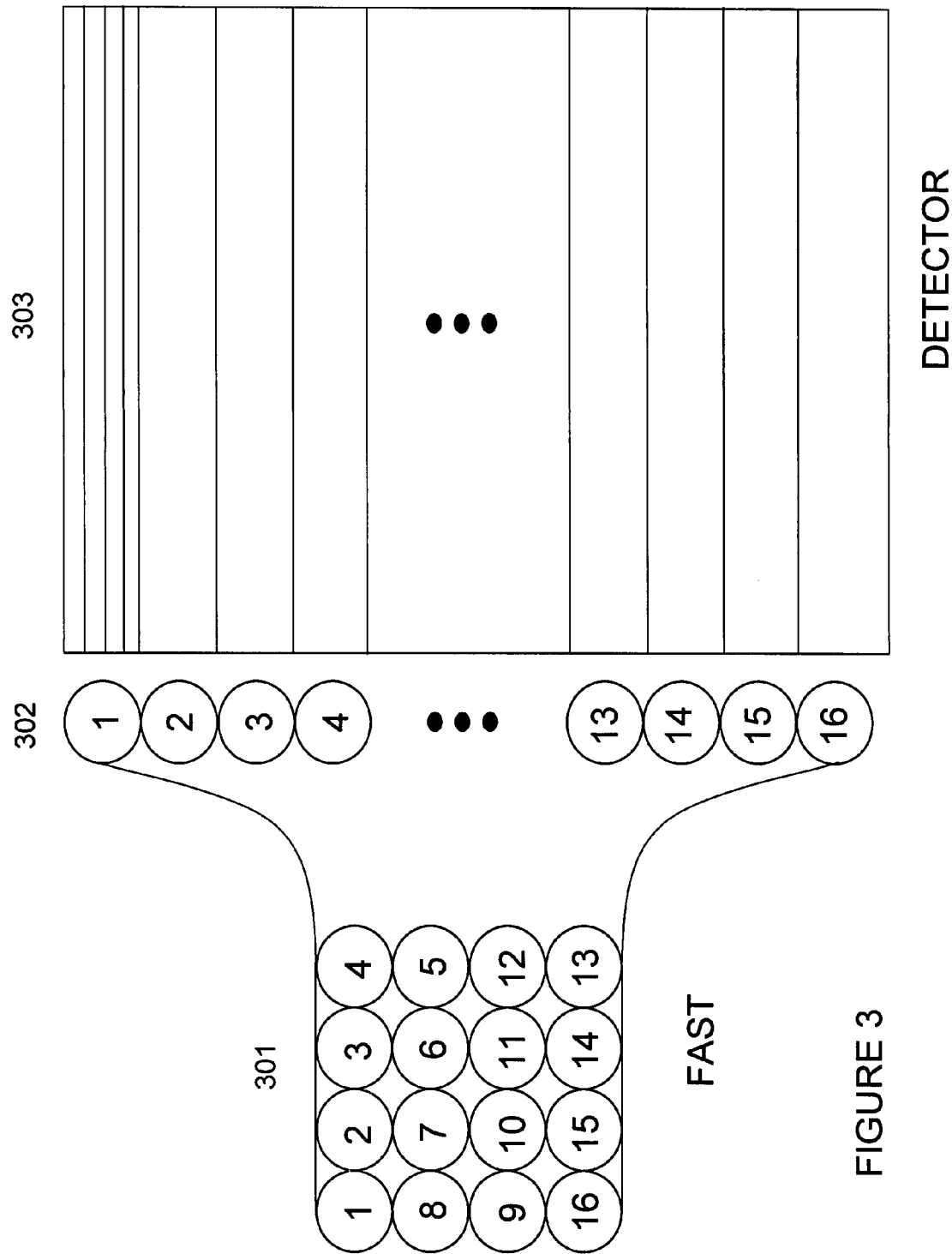
FIG. 3 is a schematic drawing of a FAST fiber layout showing an exemplary spatial mapping arrangement.

An emerging technology in the field of widefield chemical imaging is the use of fiber optic arrays. Briefly, FIG. 1 illustrates a block diagram of an exemplary Fiber Array Spectral Translator ("FAST")-based spectroscopy system. FIG. 2, on the other hand, provides a more detailed architectural view of the FAST system illustrated in FIG. 1. A FAST system may also be referred to as Dimension Reduction Arrays. FIG. 3 illustrates a simplified, exemplary, arrangement of optical fibers in a FAST fiber bundle having a two-dimensional ("2D") imaging end and a one-dimensional ("1D") distal end for feeding photons into a photon detector.

With reference now directed toward the various figures, FIG. 1 illustrates a block diagram of an exemplary FAST-based spectroscopy system including a spectrometer/detector 101, a FAST fiber bundle 102, an imaging lens 103, a collecting lens 104, a stage 105 for holding, e.g., a 96-well plate containing samples which may be a mixture containing polymorphs of a compound, a photon source 106, such as the laser shown, and a control unit 107 for controlling the spectrometer/detector 101, the photon source 106 and the stage 105. FIG. 2, on the other hand, provides a more detailed architectural view of the FAST system illustrated in FIG. 1. In FIG. 2, the system may include a spectrometer/detector 201, a FAST fiber bundle 202, which may be arranged in a substantially circular 19-fiber arrangement as shown in cross-sectional view 202a, a lens 203, which may be an imaging lens, a lens 204, which may be a collecting lens, sample 205 which may be mounted in a well of a well plate and positioned on a stage, such as the stage 105 described above with respect to FIG. 1, a photon source 206, which may be a laser as shown, a control unit 207, which may control the spectrometer/detector 201, the laser 206, and the sample 205, a filter 208 which may be a 0° filter such as a laser rejection filter, a filter 209 which may be a 7° filter, such as a laser rejection filter, a lens 210, which may be a focusing lens, and a mirror 211. A FAST system may also be referred to as a Dimension Reduction Array since, in an embodiment, the imaging end may be a 2D array and the distal end may be a 1D array. FAST technology can acquire hundreds to thousands of full spectral range, spatially resolved spectra, such as Raman spectra, simultaneously. This may be accomplished by focusing an image onto a two dimensional array of optical fibers (at the end of the fiber bundle which is proximal to the sample to be viewed) such as the FAST fiber bundle 202 which may be drawn into a one dimensional distal array (at the end of the fiber bundle which feeds the optical signals into the spectrometer/spectrograph, i.e., where the FAST fiber bundle 202 enters the spectrometer/detector 201) with serpentine (or curvilinear) ordering as illustrated in the exemplary embodiment in FIG. 3. The one dimensional fiber stack may be coupled to a spectrometer/detector 201 such as an imaging spectrograph. Software and/or hardware may then extract the spectral/spatial information that is embedded in a single CCD image frame.

Referring now to FIG. 3, the construction of the FAST array requires knowledge of the position of each fiber at both the imaging end and the distal end of the array as shown, for example, in the simplified diagram for FIG. 3 where a total of sixteen fibers are shown numbered in correspondence between the imaging (or proximal) end 301 and the distal end 302 of the fiber bundle. As shown in FIG. 3, a FAST fiber bundle may feed optical information from its 2D non-linear imaging end 301 (which can be in any non-linear configuration, e.g., circular, square, rectangular, etc., and may contain more than the 16 fibers shown in the exemplary embodiment in FIG. 3) to its 2D linear distal end 302, which feeds the optical information into associated detector rows 303. The distal end may be positioned at the input to a photon detector 303, which may include a spectrometer/spectrograph and a CCD, a complementary metal oxide semiconductor ("CMOS") detector, or a focal plane array sensor (such as InGaAs, InSb, HgCdTe ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

FIG. 3 shows a non-limiting exemplary spatial arrangement of fibers at the imaging end 301 and the distal end 302. Additionally, as shown in FIG. 3, each fiber may span more than one detector row in detector 303, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

Thus, in an exemplary FAST application, a fiber bundle may be physically organized in 2D (X-Y) at the signal input end so as to image the sample in two dimensions. On the output side, however, the fibers in the fiber bundle may be stacked in a linear or curvilinear array (1D) (principally X or Y direction only depending on the slit placement) and aligned with a slit in the grating-based spectrometer so as to facilitate extraction of spectral info. It is known that a spectrometer works on a liner (1D) input. This 1D output from the fiber bundle may be fed to the spectrometer gratings (or other similar dispersive elements) to separate signal wavelengths. Each wavelength-dispersed signal (1D) from the gratings may be sent to the CCD detector as shown in the extremely simplified view of FIG. 3. Each column of CCD pixels may represent one wavelength. There may be 5 CCD pixels (or rows) mapped to an image point (or fiber) at a particular wavelength, for example. Thus, in the case of 1024 pixels in a column, around 204-205 (1024 divided by 5) image points (or linear fiber array outputs) can be accommodated. A 1D-to-2D array mapping may then organize each column of CCD back to or close to the original 2D fiber bundle arrangement so as to obtain the 2D image of the sample for the specific wavelength (also known as a 3D spectral image).

The FAST-based chemical imaging method may provide a significant speed of analysis. Using FAST, a complete chemical imaging data set can often be acquired in approximately the amount of time it takes to generate a single spectrum from a given material with a conventional non-FAST method. Fusion of FAST-generated chemical images and high-spatial resolution images generated using other modalities can provide significant insight into the morphology and chemistry of materials. Furthermore, a FAST system may provide significant instrumentation cost reduction, expanded free spectral range (UV-IR), and optional sensitivity to polarization.

FAST enables full spectral acquisition for hundreds to thousands of spatially resolved spectra in a single image frame—dramatically increasing data acquisition rates compared to current tunable filter based technologies. Software and/or hardware may be used to extract the spatial/spectral information to reconstruct hyperspectral (chemical imaging) data cubes of the original object. Furthermore, FAST is a rugged technology that operates over an extensive spectral range (from UV to IR).

In the FAST optical system embodiment of FIG. 2, a two-lens imaging configuration is shown, although the present disclosure is not limited to such a configuration, as would be obvious to those of skill in the art. The system in FIG. 2 may include a collecting lens 204, an imaging lens 203, and some optics (e.g., filters 208 and 209, described above) for laser illumination for spectroscopy, such as Raman spectroscopy. The collecting lens 204 may be a doublet for focusing the laser beam onto the sample and collecting photons from the sample, such as Raman radiations/Raman scattered photons from the sample. The collecting lens 204 may also collimate the imaging beams (e.g., the Raman photons) and project images in infinity. The imaging lens 203 may also be a doublet and may be selected in such a way that when it is used together with the collecting lens 204, images, e.g., of Raman radiations, will be formed at its final focal plane. Because the imaging beams between the collecting lens 204 and the imaging lens 203 are collimated, it may be easier to introduce one of more laser filters, such as filters 208 and/or 209, into the FAST optics as shown in FIG. 2.

Figure 10:
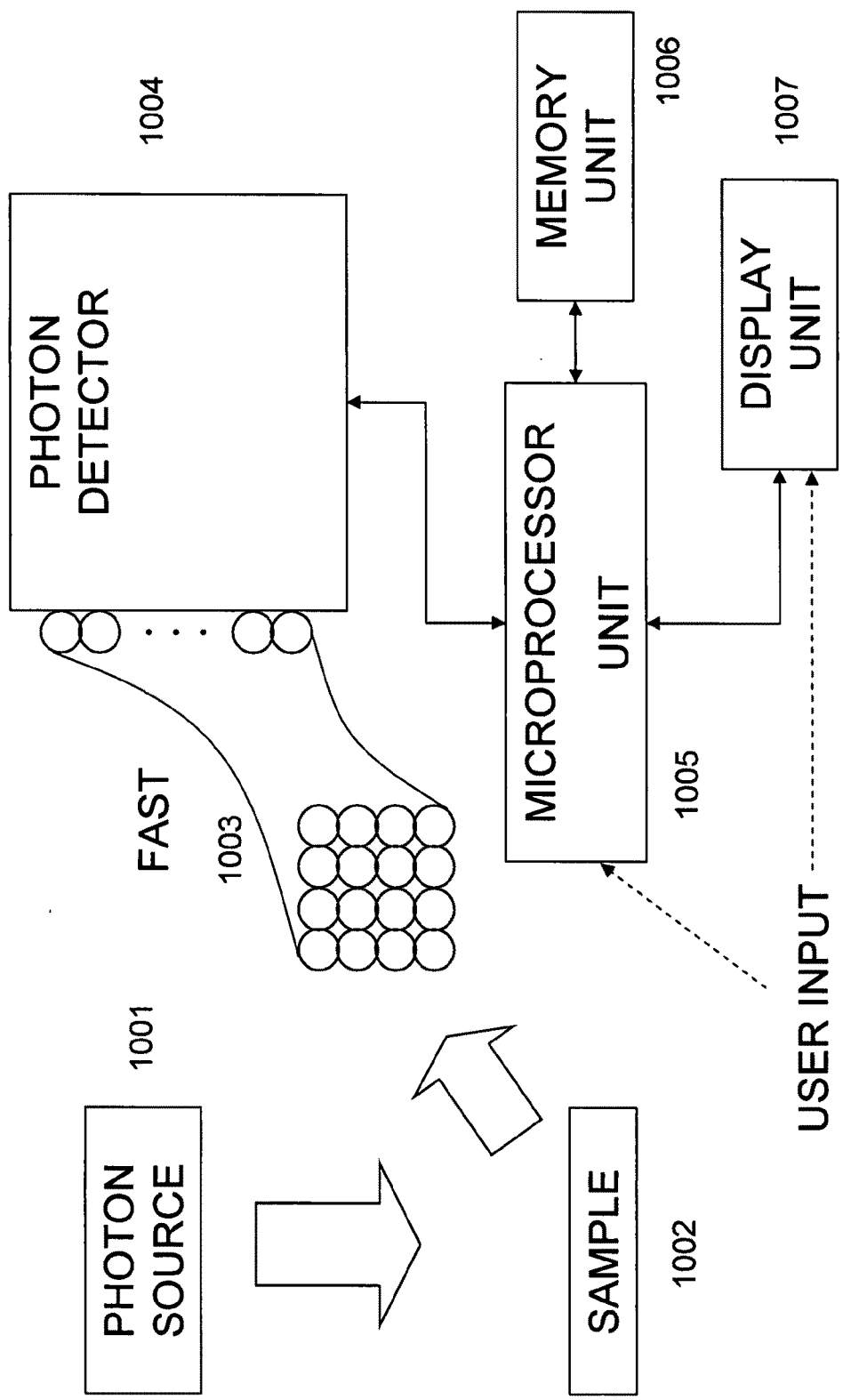
FIG. 10 is a block diagram of a FAST based spectroscopic system with optional user input according to one embodiment of the disclosure.

In one embodiment of the present disclosure, the FAST system of FIG. 1 may be used to screen or detect polymorphs present in a sample (e.g., a 96-well plate, referred to above as stage 105 in FIG. 1). The detection may be accomplished by matching spectra of the observed target sample against a set of library spectra. Thus, in case of a mixture containing polymorphs, a spectrum of a polymorph crystal may be matched against a set of library spectra of various polymorphs to identify the polymorph or polymorphs present in the mixture. In one embodiment, the library spectra of a plurality of known polymorphs of a compound may be pre-stored electronically (e.g., in a computer memory used along with the FAST system of FIG. 1, as shown in FIG. 10 discussed below). Such spectra may have been obtained in a device-independent manner (i.e., the spectra may not be taken using the FAST system selected for current polymorph screening application). In an alternative embodiment, the library spectra may be generated using the same FAST system as that being used for current polymorph screening application at hand. Hence, in such an embodiment, the library spectra may be device-dependent and, hence, may be matched more accurately with the target polymorph spectra.

In one embodiment, there may be 19 fibers in the fiber bundle. As will be obvious to those of skill in the art, the present disclosure is not limited to a 19-fiber FAST bundle and can be implemented with any number of fibers in the FAST bundle in any type of 2D orientation at the proximal, or imaging, end. The fiber bundle may be sequentially focused on each well in the 96-well plate placed on the stage 105 of FIG. 1. The stage 105 may be designed to receive samples for spectroscopic analysis. Each well may contain a plurality of polymorphs, in which case the resulting spectrum may be a combination of individual polymorph spectra. Various spectral matching techniques may be employed to identify which known polymorphs are present in the well being investigated. Also, those spectra that do not match with the library spectra may indicate presence of unknown polymorphs in the sample at hand. Such information may be useful in further analyzing the sample for detection and identification of such new polymorphs.

Figures 4A, 4B, 4C, 4D, 4E:
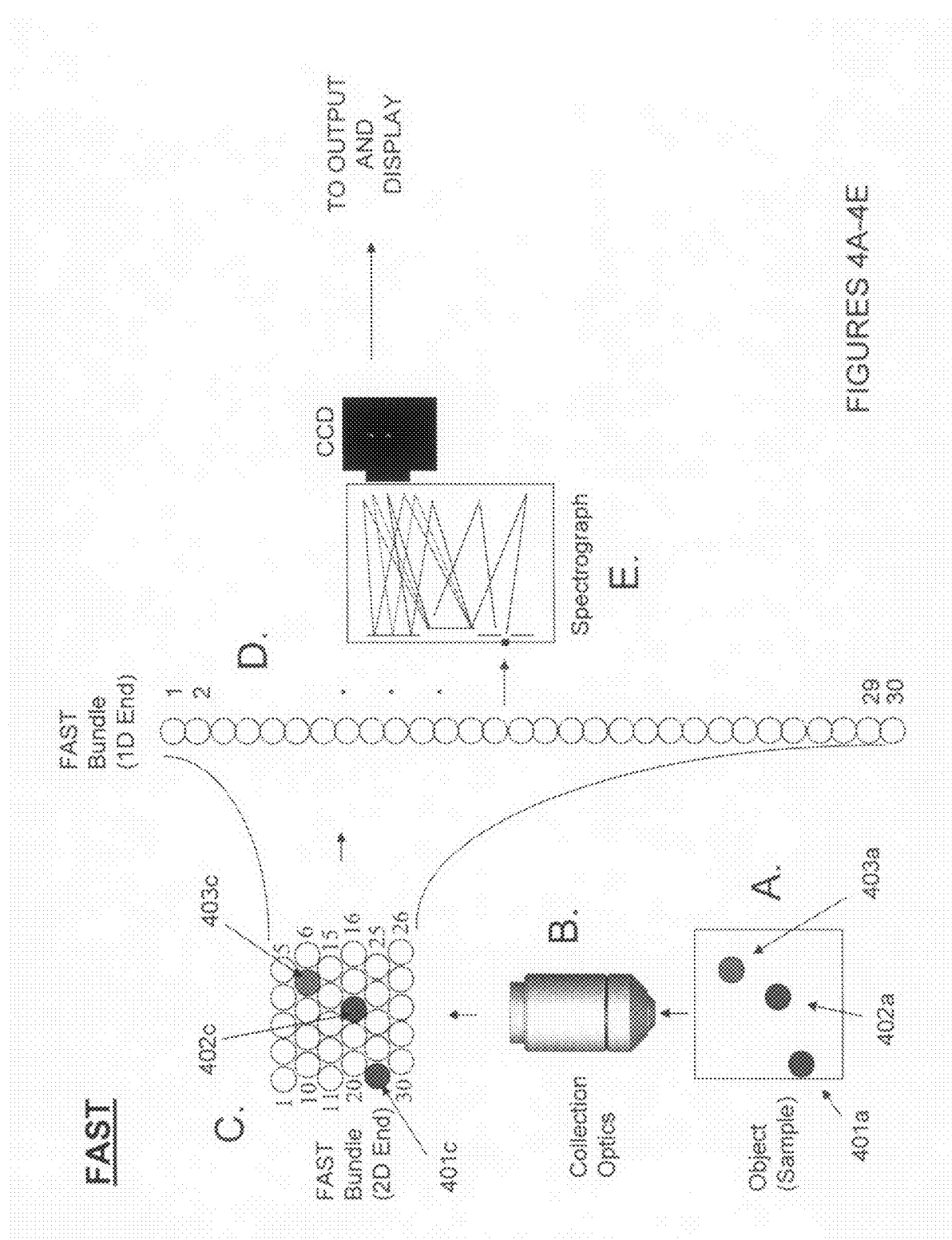
FIGS. 4A through 4H illustrate details of an exemplary FAST based spectroscopy system according to one embodiment of the disclosure.
Figures 4F, 4G, 4H:
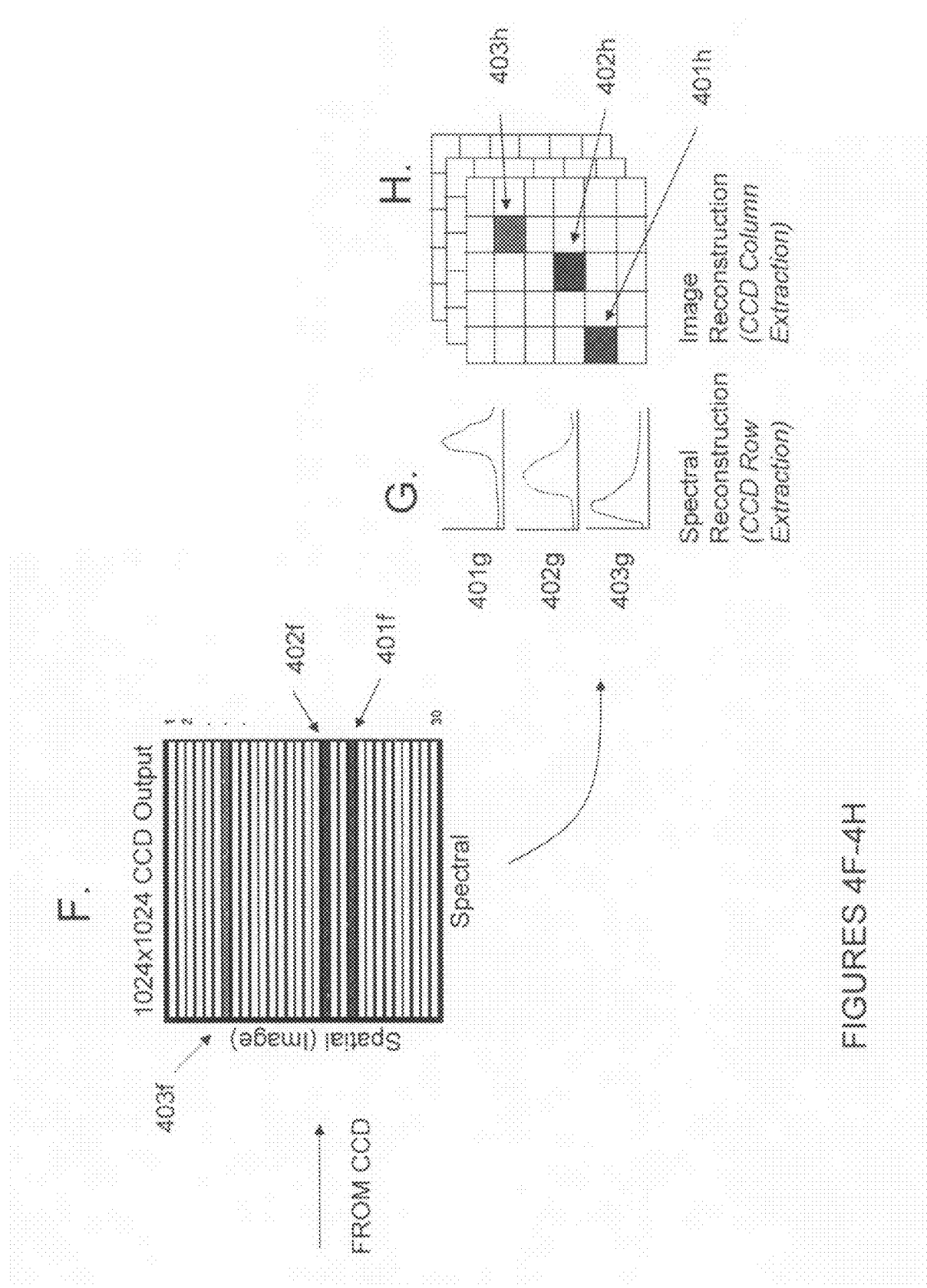

With reference now directed toward FIGS. 4A-4G, details of an exemplary FAST based spectroscopy system according to one embodiment of the disclosure are illustrated. As discussed above, FAST technology can acquire hundreds to thousands of full spectral range, spatially resolved Raman spectra simultaneously. This may be accomplished by focusing an image from a sample (FIG. 4A showing regions 401$a$, 402$a$, and 403$a$) using a light gathering optic (FIG. 4B) onto a two dimensional array of optical fibers (FIG. 4C showing regions 401$c$, 402$c$, and 403$c$ which correspond to regions 401$a$, 402$a$, and 403$a$, respectively) such as a FAST bundle, that may be drawn into a one dimensional distal array with structured (i.e., serpentine or curvilinear) or unstructured (i.e., random) ordering (FIG. 4D). The one dimensional fiber stack may be coupled to a dispersive spectrograph (FIG. 4E) which may be connected to a detector, such as the CCD shown. Software, hardware, or a combination of the two may then extract the spectral/spatial information that is embedded in a single CCD image frame (FIG. 4F showing regions 401$f$, 402$f$, and 403$f$ which correspond to regions 401$a$, 402$a$, and 403$a$, respectively) to produce spatial-specific spectra (FIG. 4G showing regions 401$g$, 402$g$, and 403$g$ which correspond to regions 401$a$, 402$a$, and 403$a$, respectively) and/or spectral-specific images (FIG. 4H showing regions 401$h$, 402$h$, and 403$h$ which correspond to regions 401$a$, 402$a$, and 403$a$, respectively) which may be displayed on an appropriate display device (e.g., a computer screen, a television, etc.). As shown in FIG. 4G, the spectral-specific spectra may be a CCD row extraction for spectral reconstruction. A 1D-to-2D array mapping may then organize each column of CCD information back to or close to the original 2D fiber bundle arrangement so as to obtain the 2D image of the sample for the specific wavelength (also known as a 3D spectral image and illustrated in FIG. 4H). As shown in FIG. 4H, the spatial-specific image may be a CCD column extraction for image reconstruction. Additionally, the display may include both a spectral reconstruction and an image reconstruction. Fiber array based chemical imaging has been demonstrated in several applications including Raman chemical imaging analysis of microcomposites and biomaterials and time-resolved atomic emission chemical imaging of laser-induced plumes.

FIGS. 5A through 5H show some exemplary uses of FAST for improved confocality for use in spectroscopic systems, such as for widefield chemical imaging. A sample shown schematically in FIG. 5A including regions 501$a$, 502$a$, and 503$a$ may be illuminated globally (FIG. 5B), i.e., an entire area of the sample (or the entire sample) is illuminated, illuminated in a point-focused manner (FIG. 5C) where only one point or region of the sample is illuminated, in FIG. 5C region 502C is the only illuminated region of the sample, or randomly (FIG. 5D) where only the three regions 501$d$, 502$d$, 503$d$ of the sample are illuminated. Regions 501'$x$', 502'$x$', and 503'$x$' throughout FIGS. 5A through 5H, where '$x$' represents 'a' through 'h', are corresponding regions, respectively. Returning to FIG. 5C, the region 502$c$ is the only illuminated region of the sample and this may be achieved numerous ways including structured fiber optic illumination using a FAST-based spectroscopic system with or without the use of optical lenses. In an embodiment, regions 501$a$, 502$a$, and 503$a$ may represent three exemplary fibers in a fiber bundle of a FAST system (e.g., the FAST system of FIG. 1). It is observed here that the optical confocality of a measurement may be improved when combined with the use of FAST as discussed herein.

Figures 5A, 5B, 5C, 5D:
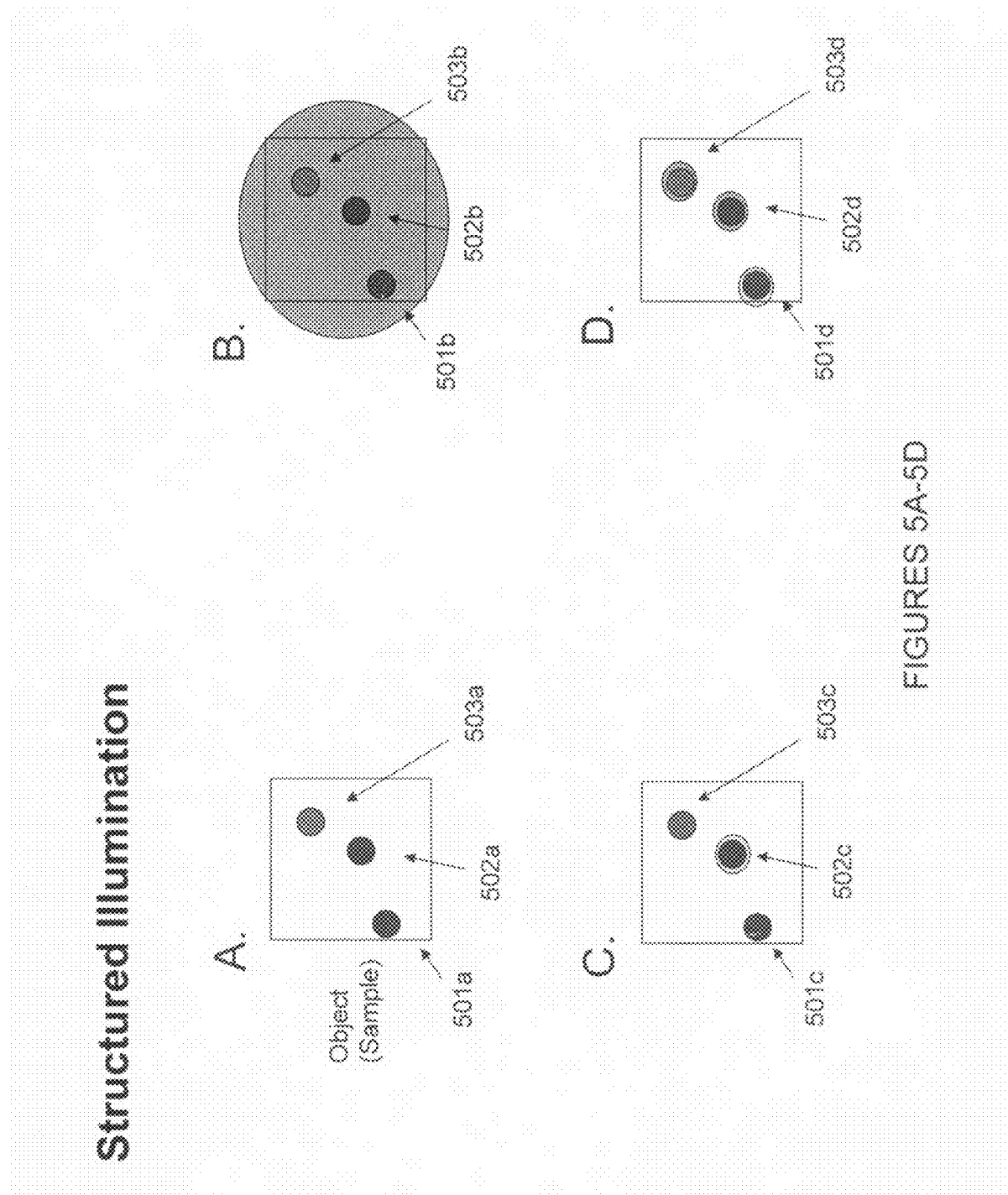
FIGS. 5A through 5D illustrate different structured illumination arrangements in a FAST based spectroscopy system according to embodiments of the disclosure.
Figures 5E, 5F, 5G, 5H:
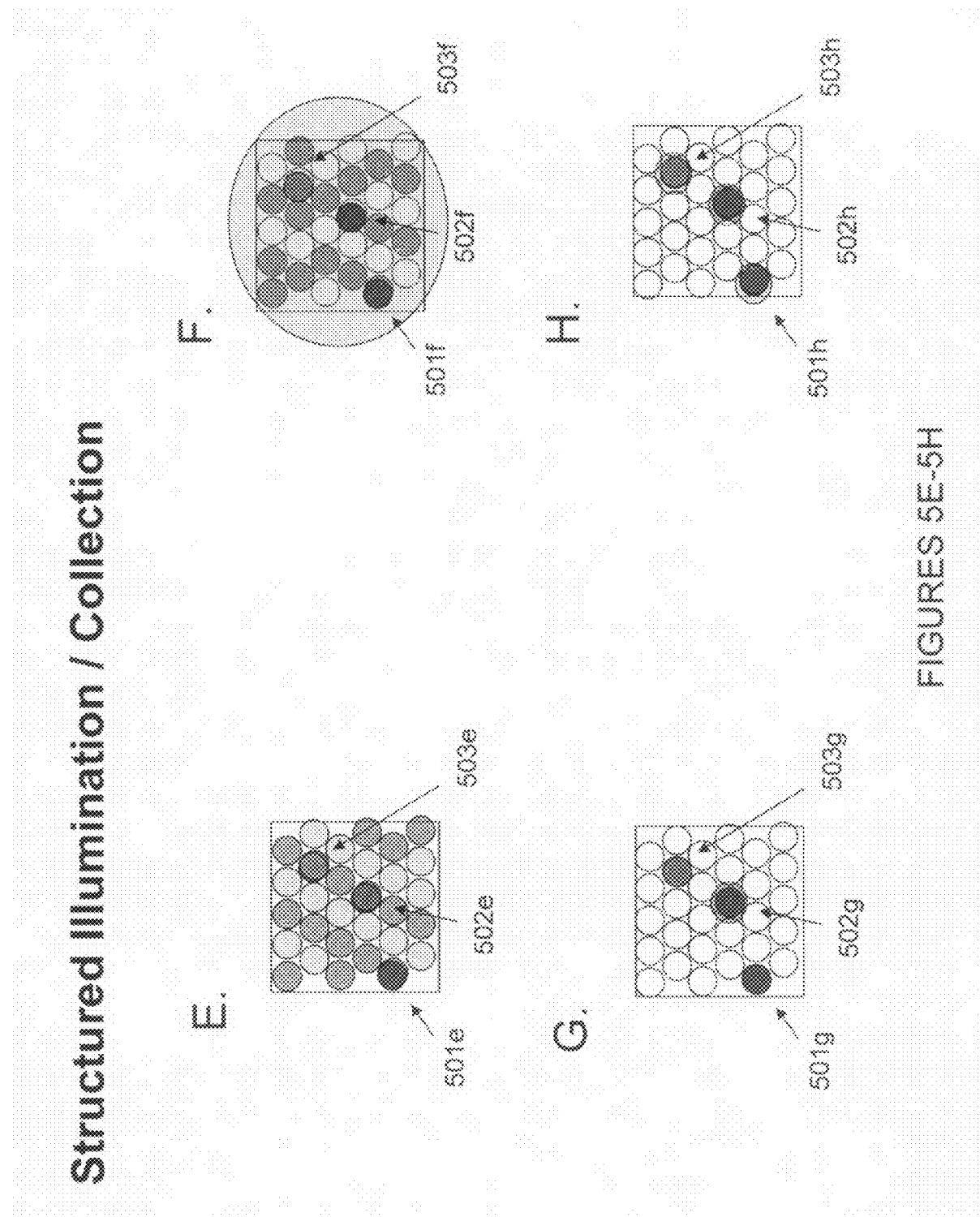
FIGS. 5E through 5H illustrate different structured illumination and collection arrangements in a FAST based spectroscopy system according to embodiments of the disclosure.

In FIG. 5E, the illumination of and collection of light from the sample is achieved with through the same fiber. In other words, the illumination and collection optics is the same—the fibers in the single fiber bundle in the FAST system—in the embodiment of FIG. 5E. Specifically, FIG. 5E shows a 30 fiber FAST bundle, such as the one illustrated in FIG. 4C, where the illuminating light travels through each of the 30 fibers to illuminate the sample and each of the 30 fibers receives light from the sample and directs that received light to, for example, a photon detector. An embodiment of the disclosure contemplates, but the disclosure is not limited to, a situation where the illumination region and the collection region for any one fiber is mutually exclusive of the illumination region and the collection region of the other fibers in the FAST bundle. In the configuration shown schematically in FIG. 5F, the sample is globally illuminated (with an illumination source, e.g., an angled laser as shown in FIG. 2 or via a dispersive fiber) that is different from the light collection mechanism (i.e., one or more fibers in the fiber bundle of the FAST system) and light is gathered with all fibers within the FAST bundle. In FIG. 5G, the illumination is restricted to a small area around region 502g and the light is gathered from an individual fiber (e.g., the fiber represented by the circle 502g in FIG. 5G) or a smaller number of fibers consistent with the geometry and size of an object of interest in the sample. The illumination in FIG. 5G may be accomplished using a laser as shown, for example, in FIGS. 1 and 2, or using one or more fibers in the fiber bundle of the FAST (in which case the illumination source and the light collection source may be the same). In FIG. 5H, the illumination is structured and restricted to areas of interest (i.e., 501h, 502h, and 503h) within the sample while the collected radiation is primarily captured by a restricted number of fibers in the FAST bundle (corresponding to areas 501h, 502h, and 503h). In the embodiment of FIG. 5H, the structured illumination optics may include a laser coupled with an optical switch or a pattern creation optics to accomplish the desired structured illumination. The structured illumination can be accomplished either sequentially or simultaneously (i.e., in parallel). It is noted here that various illumination and collection approaches illustrated in FIGS. 5A through 5H may be part of a non-destructive imaging system of, for example, a chemical or biological sample.

FIGS. 6-8 show real data collected using a prototype FAST system configured as shown schematically in FIG. 5F. A multilayer polymer standard (shown schematically in FIG. 6A) with known layer thicknesses was analyzed depth-wise using a FALCON™ Raman chemical imaging system marketed by ChemImage Corporation of Pittsburgh, Pa., wherein the FALCON™ system was equipped with a 64-fiber FAST bundle. Spectra at various sample depths were acquired using the FAST bundle and compared. The spectra from the light collected from all fibers were compared to the spectra obtained from a single fiber (FIGS. 6B-6D). In each of the FIGS. 6B-6D, the top spectrum in the respective graph is obtained using a FAST single fiber and the bottom spectrum is obtained using the entire FAST bundle of 64 fibers. The axes of the graphs in FIGS. 6B-6D Raman Shift in wavenumbers for the horizontal axis and Intensity (in arbitrary units) for the vertical axis. It is observed here with reference to FIG. 6A that the multilayer polymer standard included the following layers of materials: the top layer 601 is Polyethylene Terephthalate ("PET"), the next layer down 602 is an adhesive layer following the PET layer, the middle layer 603 is an Ethylene Vinyl Alcohol ("EV-OH") copolymer, the next layer down 604 is another adhesive layer following the EV-OH layer, and the bottom layer 605 is Low Density Polyethylene ("LD PE") and Titanium Dioxide ("$TiO_2$"). The thicknesses of the layers are shown in FIG. 6A.

As is known in the art, the depth analysis represented in FIGS. 6-8 may be accomplished by obtaining a spectrum at a specific layer of the polymer standard and then moving the stage (item 105 in FIG. 1) holding the sample containing the polymer standard sample upward so as to enable the collecting optics to image the next successive layer. It is noted that using a single fiber from FAST effectively limits the area/volume from which the light is gathered. The data collection from the single fiber was accomplished by restricting the rows from which data was collected from the spectrometer CCD as discussed later hereinbelow with reference to FIG. 9. As can be seen in each of FIGS. 6B (PET), 6C (EVOH), and 6D (LDPE&TiO2) that the peaks in the spectra for the single FAST fiber case (spectra 606b, 606c, and 606d) are generally thinner than the peaks in the spectra for the 64 FAST fiber case (spectra 607b, 607c, and 607d), which indicates that the single FAST fiber case has an increased confocality over the 64 FAST fiber case.

Figure 7A:
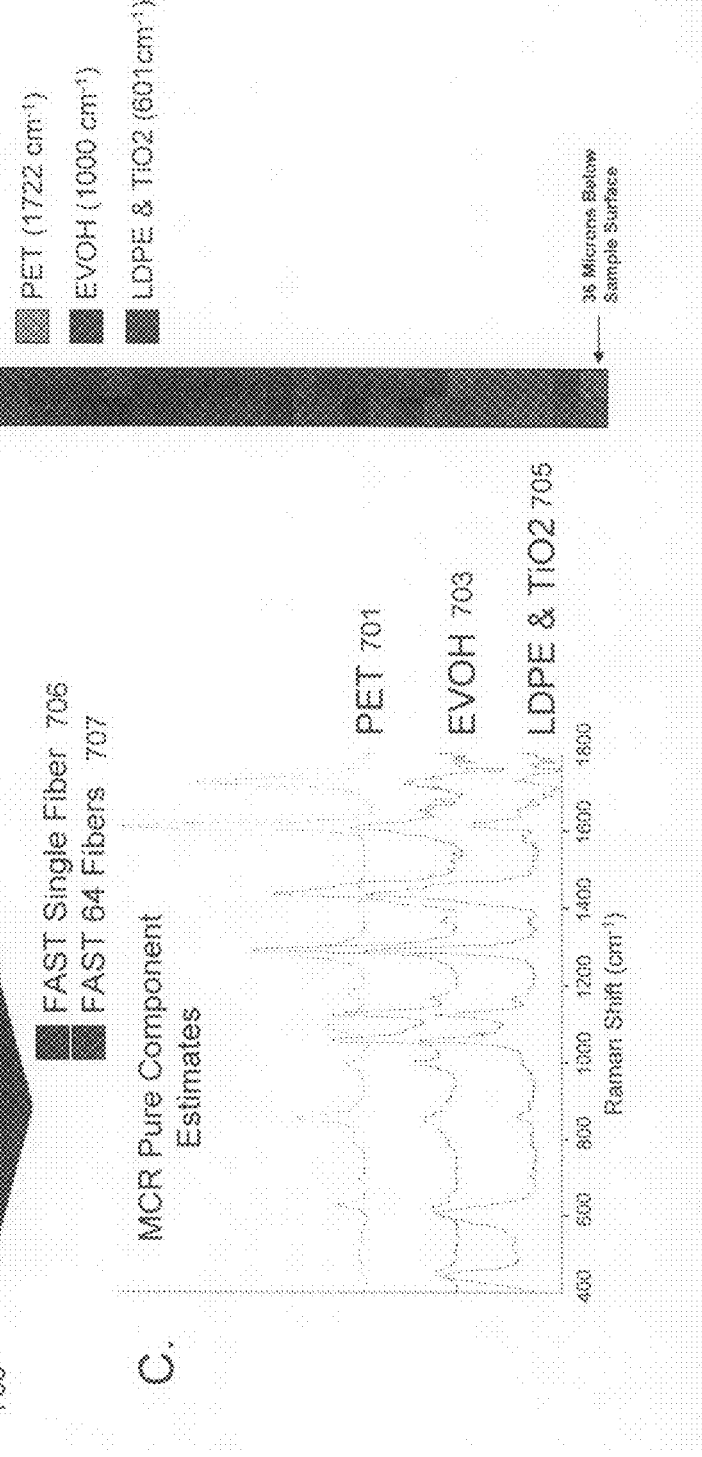
FIGS. 7A through 7C illustrate a test sample (FIG. 7A), a comparison of data using FAST single fiber and FAST multiple fibers (FIG. 7B), and a graph (FIG. 7C) showing data collected from the test sample using a FAST based spectroscopy system according to an embodiment of the disclosure.
Figure 7B:
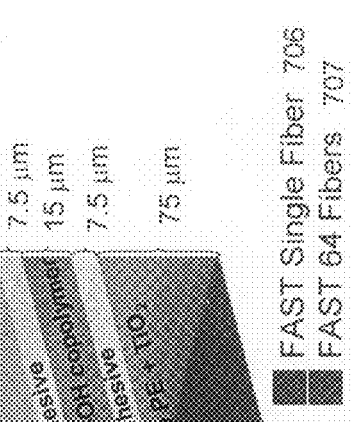
Figure 7C:
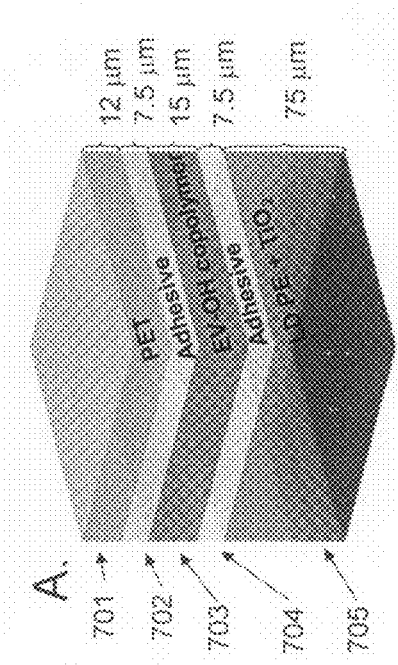

Referring now to FIGS. 7A-7C, FIG. 7A illustrates the same multilayer polymer standard illustrated in FIG. 6A which includes the following layers of materials: the top layer 701 is Polyethylene Terephthalate ("PET"), the next layer down 702 is an adhesive layer following the PET layer, the middle layer 703 is an Ethylene Vinyl Alcohol ("EV-OH") copolymer, the next layer down 704 is another adhesive layer following the EV-OH layer, and the bottom layer 705 is Low Density Polyethylene ("LD PE") and Titanium Dioxide ("$TiO_2$"). The thicknesses of the layers are shown in FIG. 7A. FIG. 7B exemplifies a false-color, depth-wise reconstruction of the FAST data comparing the two modes of detection (single fiber 706 vs. the entire 64-fiber bundle 707) where the upper sample surface (i.e., the top surface of the PET layer 701) is at the top of the reconstruction and the bottom of the reconstruction is 36 microns below the upper sample surface (as measured by movement of the stage upon which the sample rests). FIG. 7C shows spectra depicting Multivariate Curve Resolution (MCR) pure component estimates for PET (701), EVOH (703), and LDPE+$TiO_2$ (705) layers from the data obtained in the single fiber mode of detection 706. As can be seen from FIG. 7B, the FAST single fiber case shows much sharper distinction between the layers than the FAST 64 fiber bundle case. Therefore, the FAST single fiber case allows for more specific readings throughout the sample than the FAST 64 fiber bundle case.

Referring now to FIGS. 8A-8D, FIG. 8A illustrates the same multilayer polymer standard illustrated in FIG. 6A which includes the following layers of materials: the top layer 801 is Polyethylene Terephthalate ("PET"), the next layer down 802 is an adhesive layer following the PET layer, the middle layer 803 is an Ethylene Vinyl Alcohol ("EV-OH") copolymer, the next layer down 804 is another adhesive layer following the EV-OH layer, and the bottom layer 805 is Low Density Polyethylene ("LD PE") and Titanium Dioxide ("$TiO_2$"). The thicknesses of the layers are shown in FIG. 8A. FIGS. 8B-8D show Raman intensity plots for three layers differing in composition in the multilayer polymer system of FIG. 8A. The plots in FIGS. 8B-8D are as a function of sample depth (movement of the stage on which the sample rests) in microns as the horizontal axis with a normalized intensity value as the vertical axis. The layer-specific wavelength is also indicated along with the respective layer material in FIGS. 7B-7D. The reduced full-width at half maximum ("FWHM") plot for the FAST single fiber (e.g., FWHM=8 in FIG. 8C) when compared to the 64 fibers (e.g., FWHM=9 in FIG. 8C) is an indication of the enhanced confocality that the FAST single fiber measurement provides. It is anticipated for configurations in which the illumination is structured (e.g., as shown in FIGS. 5A-5D) in addition to the structured collection (e.g., as shown in FIGS. 5G-5H) that further/additional confocality improvement may be achieved since the structured illumination/structured collection case further restricts the illumination and sampling volumes of the sample.

Figures 9A, 9B, 9C, 9D, 9E, 9F:
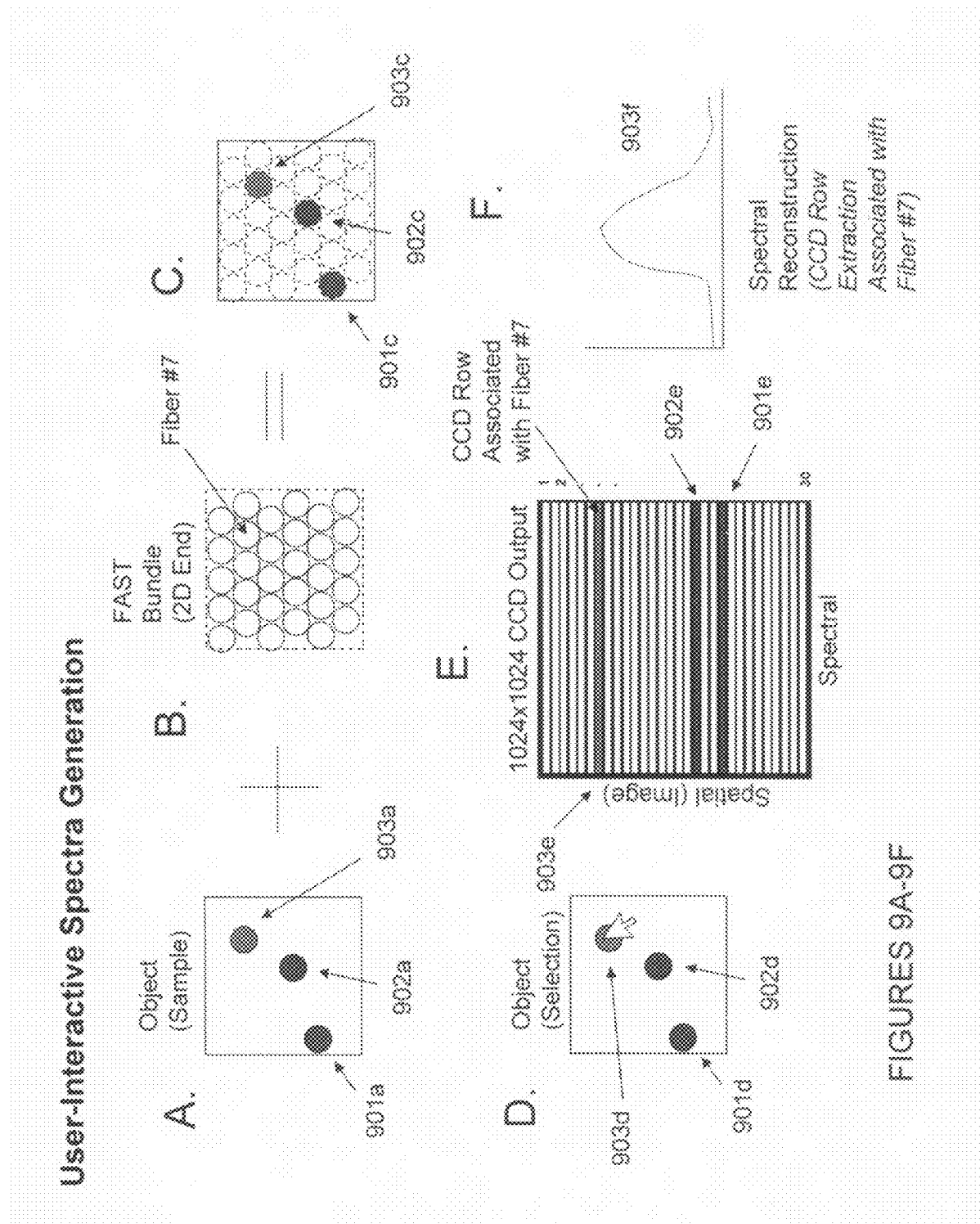
FIGS. 9A through 9F illustrate a method using a FAST based spectroscopy system according to one embodiment of the disclosure for real-time or near real-time user-interactive generation of spectra from one or more spatial locations on a sample.

FIGS. 9A through 9F illustrate a further method of FAST for enabling a real-time or near real-time user-interactive means of generating spectra associated with one or more spatial locations within an image. FIG. 9A illustrates a sample including regions 901a, 902a, and 903a. A FAST image is gathered from the sample using a plurality of fiber optics (FIG. 8B). In one embodiment, the illumination and collection in FIG. 9B is similar to the approach depicted in FIG. 5F and described above. In another embodiment, the illumination and collection in FIG. 9B may be accomplished using the approach depicted in FIG. 5E and described above. The fiber optics within the FAST bundle are addressable (in software, hardware, and/or a combination of the two) to respective spatial locations on the sample and image data from the fibers are captured using one or more detectors. In one embodiment, each fiber in the fiber bundle may be linked (or mapped) through software, hardware, or a combination of software and hardware with a respective spatial location or region in the sample (e.g., regions 901c, 902c, and 903c, which correspond to regions 901a, 902a, and 903a, respectively), and the spectral data collected by each fiber may be captured by that row(s) in the CCD detector which may be associated with that specific fiber. In one embodiment, a user may select one or more spatial locations from a computer-displayed image of the sample with the use of a computer keyboard, mouse and/or touch screen (as represented by the large arrow in FIG. 9D selecting region 903d). A computer-displayed optical image of the sample may be generated using a video camera or CCD-based imaging device (different from the CCD detector with the spectrograph) (not shown) that may be placed along the optical path of collection optics to record an optical image of the sample as is known in the art. Because of the known spatial linking between various sample regions and corresponding fibers, and availability of information on association of various CCD rows with their respective fibers, the operative software, hardware, or combination of software/hardware may be then configured to collect data from only that portion of the FAST detector image (FIG. 9E) which is associated with the spatial location(s) selected by the user. Referring to FIGS. 9B-9F, fiber #7 in the FAST bundle (FIG. 9B) is selected by the user (FIG. 9D) such that the associated row in the CCD (FIG. 9E) is displayed on an imaging device (FIG. 9F). Such selective or structured collection of spectral data allows the software, hardware, or combination of software/hardware to generate a representative spectrum (or spectra) of only the user-selected spatial location(s) as illustrated by spectrum 903f in FIG. 8F. Thus, although the sample may be globally illuminated and although each fiber in the fiber bundle (which is a 30-fiber bundle in the exemplary embodiment of FIG. 9B as in the embodiment of FIG. 4C) may be collecting optical information from the sample and sending that information to the CCD detector, the software, hardware, or combination of software and hardware may be configured to collect (from the CCD detector) only that spectral information which is associated with the sample spatial location/region selected by the user. Such user-interactive spectrum/spectra (e.g., Raman spectra) generation may facilitate real-time or near real-time probing of sample regions of interest.

In one embodiment, such selective spectrum generation approach may be extended to include overlaying (not shown) the optical image (generated using, e.g., a video camera) with a false-colored FAST image (e.g., a Raman chemical image) that is generated based on a correlation between the spectral signatures produced in real-time with FAST and a library of known spectral signatures. This allows the user to visualize the sample chemistry in real-time.

With reference now directed towards FIG. 10, an exemplary system according to an embodiment of the present disclosure is illustrated in block diagram form. A photon source 1001 may illuminate with first photons a sample 1002, which may contain polymorphs of a compound, to thereby produce second photons. The photon source 1001 may be any typical photon source used for spectrographic purposes, such as a laser, white light source, UV (ultraviolet) lamp, etc. A fiber array spectral translator 1003, having plural fibers receives the second photons and directs them to a photon detector 1004 which is operatively connected to the fiber array spectral translator. The photon detector 1004 may include a dispersive spectrograph (not shown) or other similar equipment as is known in the art. The photon detector 1004 detects the second photons to thereby obtain a first spectrum. A microprocessor unit 1005 is operatively connected to the photon detector 1004 and to a memory unit 1006. The memory unit 1006 may store a set of second spectra where each spectrum of the set of second spectra may be representative of a different polymorph of the compound (sample 1002). The microprocessor unit 1005 may compare the first spectrum with the set of second spectra to thereby determine the presence of one or more polymorphs in the mixture based on said comparison. A display unit 1007 may be operatively connected to the microprocessor unit 1005 for displaying spectra and/or images generated from the photons detected by the photon detector 1004. Optionally, the microprocessor 1005 and/or the display unit 1007 may be adapted to accept user input, such as via a computer mouse or pointing device, a keyboard, or, in the case of the display unit 1007, a touchscreen. The user input, as described above, may include user selection of specific information for display of specific spectra and/or images.

Figure 11A:
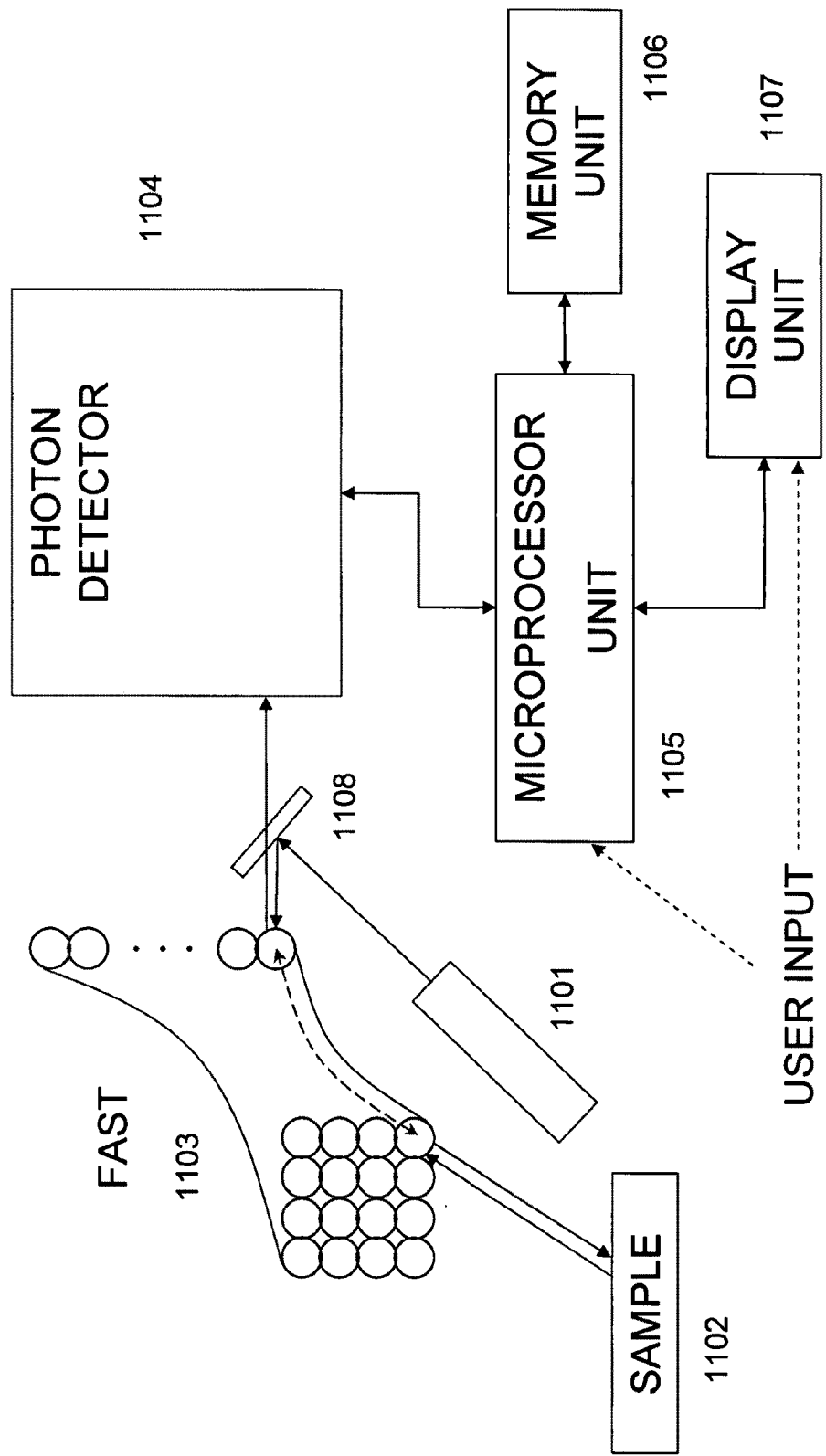
FIG. 11A is a block diagram of a FAST based spectroscopic system with optional user input according to one embodiment of the disclosure.
Figure 11B:
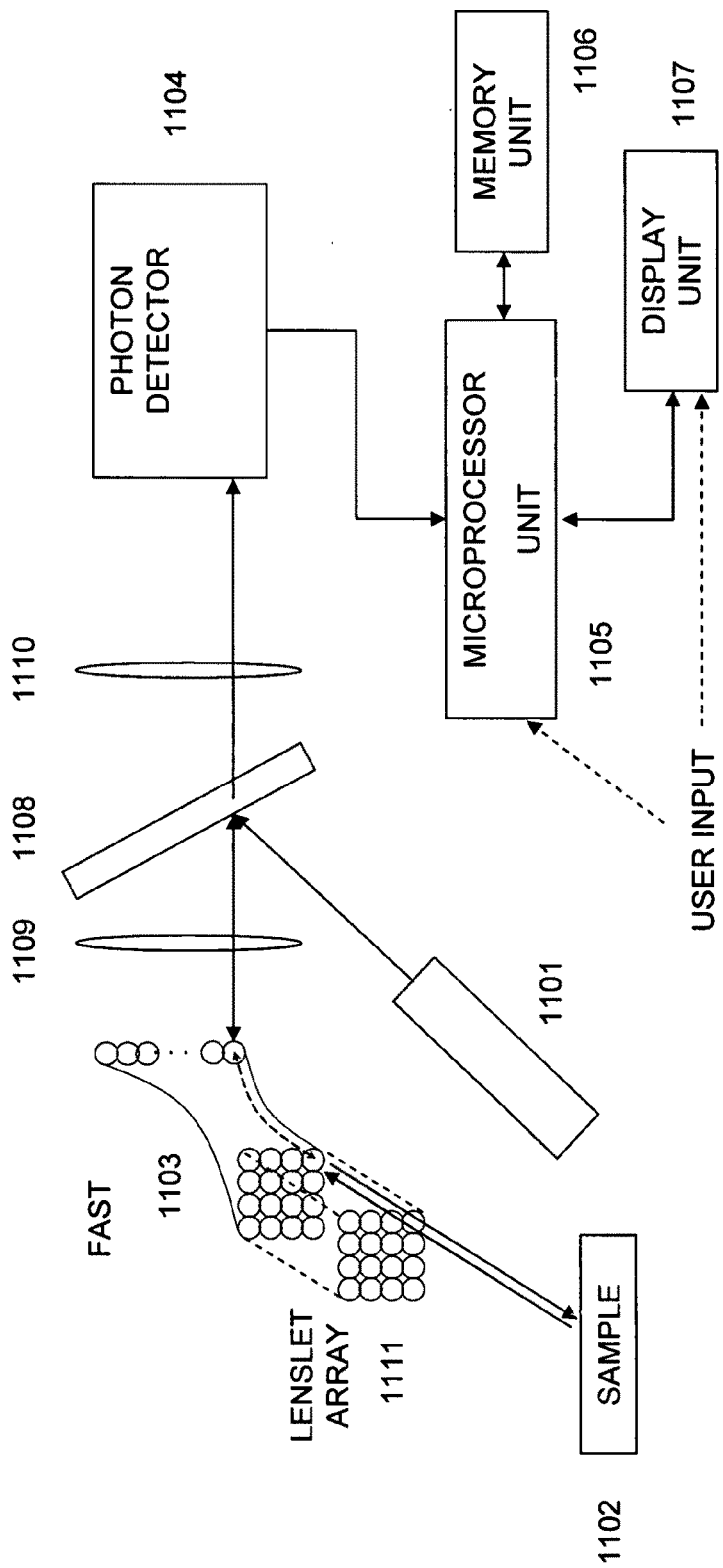
FIG. 11B is a block diagram of a FAST based spectroscopic system with optional user input according to another embodiment of the disclosure.

FIGS. 11A and 11B show further embodiments of systems as described above and with respect to FIG. 10, like reference numbers refer to like devices. FIG. 11A illustrates an exemplary system for a single FAST fiber illumination and collection arrangement where the output of the photon source 1101 is directed to a source rejection filter 1108, such as a laser rejection filter, dichroic beamsplitter, or similar device, such that the illuminating photons rejected by the filter (i.e., reflected) are focused onto a single fiber of the 1D end of a FAST bundle. The illuminating photons are then delivered to the sample 1102 at the 2D end of the FAST bundle where they, for example, interact with the sample 1102 to generate, second (e.g., scattered) photons which are then gathered by the same fiber in the FAST bundle and directed towards the photon detector 1104. FIG. 11B illustrates a further embodiment which includes a first lens 1109, a second lens 1110, and a lenslet array 1111. In this embodiment, the rejected (i.e., reflected) photons from the photon source 1101 are focused onto a single fiber of the 1D end of a FAST bundle via lens 1109. The illuminating photons are delivered to the sample 1102 at the 2D end of the FAST bundle. A lenslet array 1111 may be coupled to the 2D end of the FAST array for improved efficiency in delivering and collecting the illuminating photons and the second (e.g., scattered, or Raman scattered) photons. The collected second photons (e.g., reflected/scattered source light, scattered light from sample, emitted light from sample, etc.) are collimated by lens 1109 and filtered by the source rejection filter 1108. The photons emitted/scattered by the sample that pass through the source rejection filter 1108 are focused onto the entrance slit of a spectrograph/photon detector 1104 via lens 1110.

Figure 12:
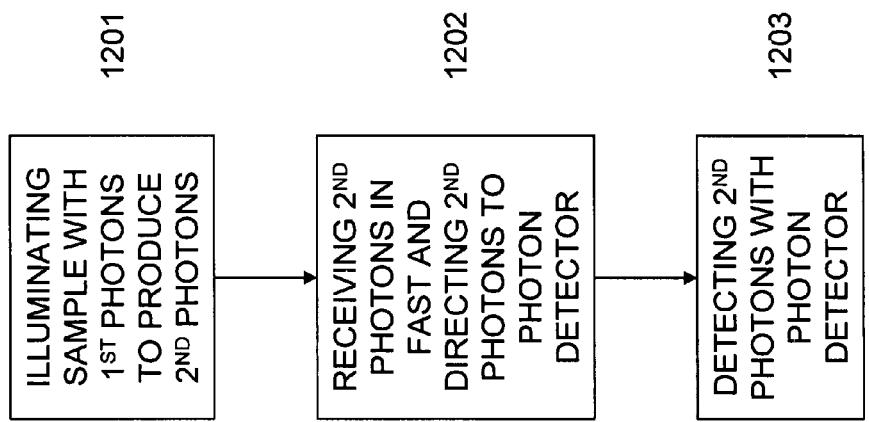
FIG. 12 is a flow chart of a method for detecting photons using a FAST based spectroscopic system according to an embodiment of the disclosure.

FIG. 12 is a flow chart of a method for detecting photons using a FAST based spectroscopic system according to an embodiment of the disclosure. At block 1201, a sample is illuminated with first photons to produce second photons. In an embodiment, the second photons may be fluorescent photons from the sample without the need to illuminate the sample with the first photons. At block 1202, the second photons are received at the 2D end of a FAST bundle and the second photons are directed towards a photon detector (which may typically include a spectrograph, as is known in the art) where the second photons are detected by the photon detector at block 1203.

Figure 13:
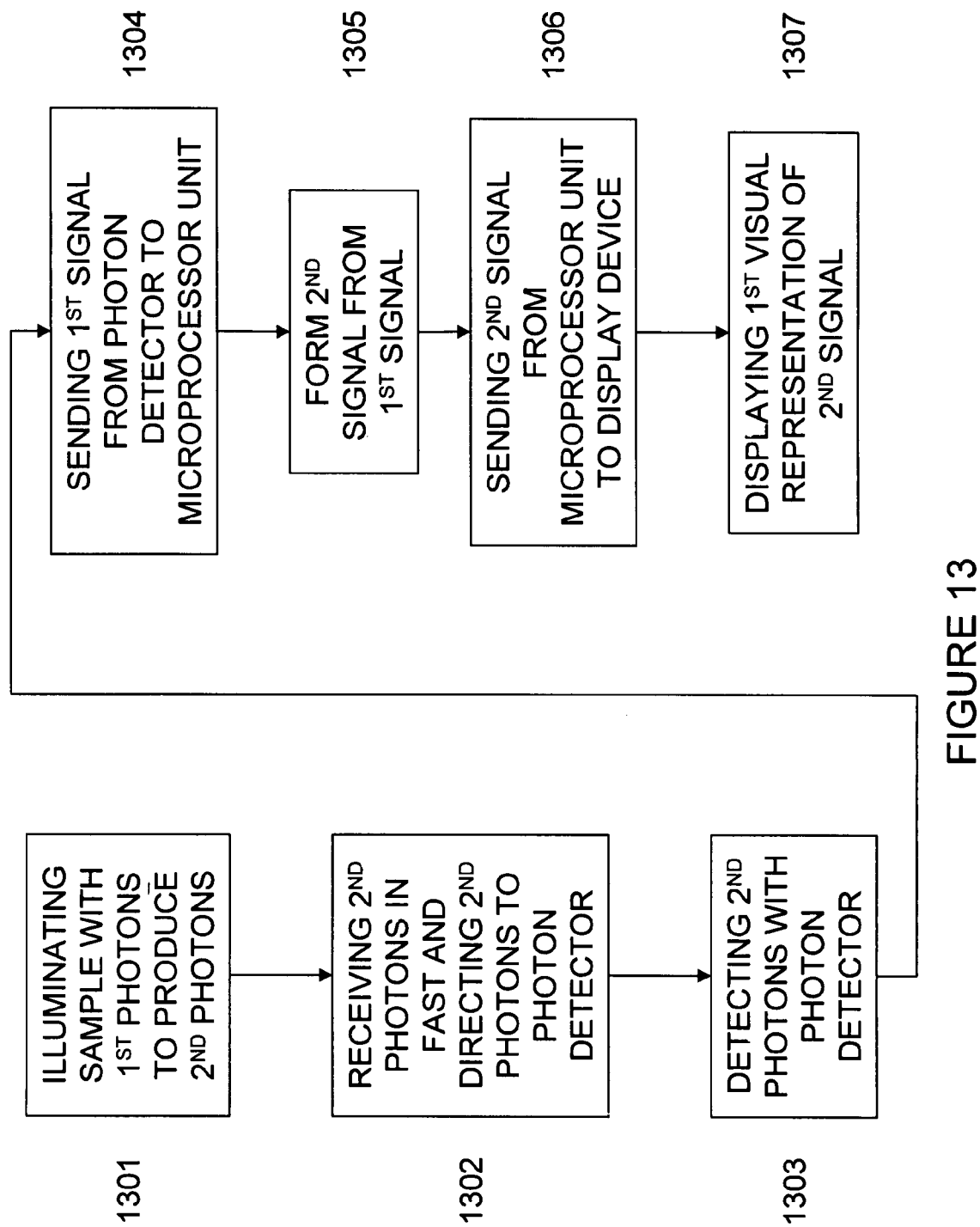
FIG. 13 is a flow chart of a further method for detecting photons using a FAST based spectroscopic system and displaying a visual representation of the detected photons according to an embodiment of the disclosure.

FIG. 13 is a flow chart of a further method for detecting photons using a FAST based spectroscopic system and displaying a visual representation of the detected photons according to an embodiment of the disclosure. Blocks 1301, 1302, and 1303 correspond to blocks 1201, 1202, and 1203, respectively, as described above. At block 1304, a signal is sent by the photon detector to a microprocessor unit. The signal may be representative of the second photons detected by the photon detector. At block 1305, the microprocessor unit may then form a second signal based on the received first signal and, at block 1306, send the second signal from the microprocessor unit to a display device. Alternatively, the microprocessor unit may simply relay the signal from the photon detector to the display device with little or no change to the signal from the photon detector. At block 1307, the display device may display a visual representation of the signal from the microprocessor unit (e.g., the second signal).

Figure 14:
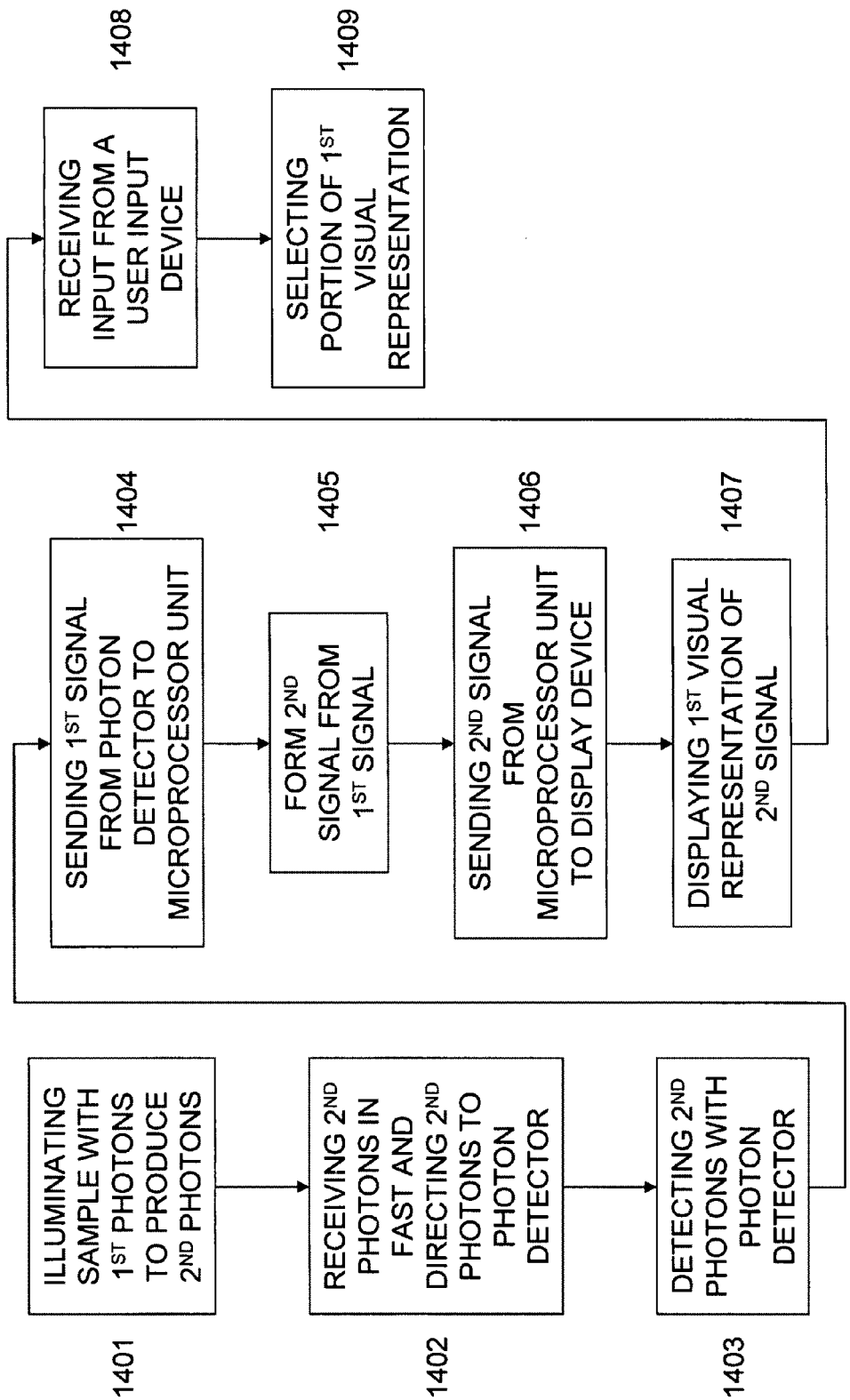
FIG. 14 is a flow chart of a further method for detecting photons using a FAST based spectroscopic system, displaying a visual representation of the detected photons, and selecting a portion of the visual representation based on user input according to an embodiment of the disclosure.

FIG. 14 is a flow chart of a further method for detecting photons using a FAST based spectroscopic system, displaying a visual representation of the detected photons, and selecting a portion of the visual representation based on user input according to an embodiment of the disclosure. Blocks 1401 through 1407 correspond to blocks 1301 through 1307, respectively, as described above. At block 1408, an input is received from a user via a user input device, such as, e.g., a computer mouse, pointing device, keyboard, or touch-screen. The input may be a user-requested selection, at block 1409, of a specific spectra and/or image to be displayed on the display device, as discussed above.

Figure 15:
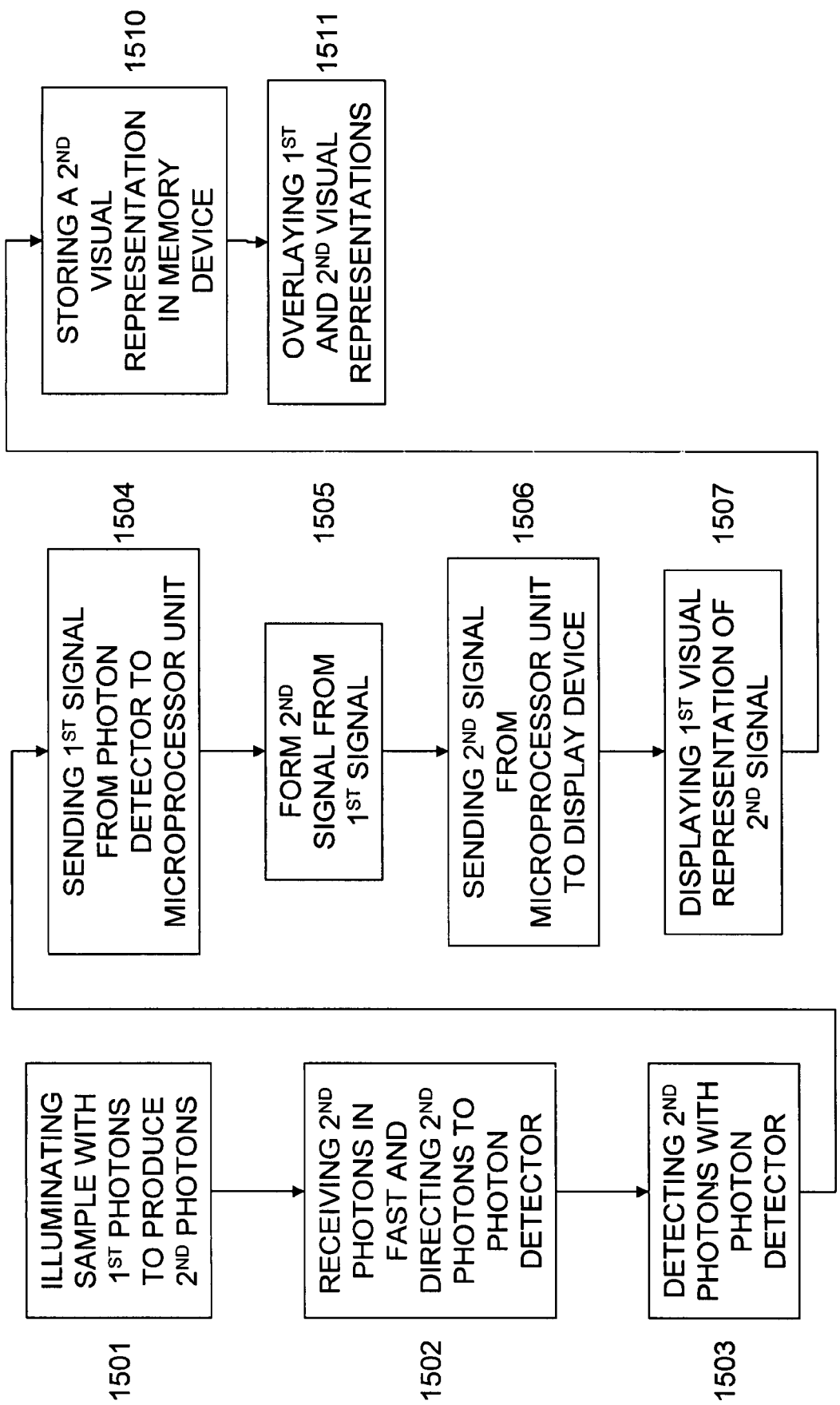
FIG. 15 is a flow chart of a further method for detecting photons using a FAST based spectroscopic system, displaying a visual representation of the detected photons, storing a second visual representation in a memory device, and overlaying the two visual representations according to an embodiment of the disclosure.

FIG. 15 is a flow chart of a further method for detecting photons using a FAST based spectroscopic system, displaying a visual representation of the detected photons, storing a second visual representation in a memory device, and overlaying the two visual representations according to an embodiment of the disclosure. Blocks 1501 through 1507 correspond to blocks 1301 through 1307, respectively, as described above. At block 1510, a second visual representation of a spectrum and/or image may be stored in a memory device. At block 1511, the second visual representation may be overlaid with a first visual representation such as the visual representation discussed above with respect to block 1307 in FIG. 13. This overlaying of visual representations may be performed with or without user input, such as the user input described with respect to blocks 1408 and/or 1409 in FIG. 14.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

We claim:

1. In a system for detecting photons from a sample wherein a first portion of said sample is illuminated by first photons from a photon source whereby an interaction between said first photons and said sample produces second photons, and wherein said second photons are received by substantially all of the optical fibers in a fiber array spectral translator, and wherein said second photons are directed by said substantially all of the optical fibers in said fiber array spectral translator to a photon detector which detects said second photons, the improvement comprising increasing the confocality of said system by directing only said second photons in a predetermined group of said plural fibers to said photon detector, wherein each fiber in said predetermined group is associated with a predetermined different second portion of said sample wherein each of said predetermined different second portions is smaller than said first portion.

2. The system of claim 1 wherein a number of fibers in said predetermined group is less than or equal to twenty-five percent of a total number of fibers in said fiber array spectral translator.

3. The system of claim 1 wherein a number of fibers in said predetermined group is less than or equal to ten percent of a total number of fibers in said fiber array spectral translator.

4. The system of claim 1 wherein a number of fibers in said predetermined group is less than or equal to one percent of a total number of fibers in said fiber array spectral translator.

5. The system of claim 1 wherein ones of said predetermined different second portions overlap.

6. The system of claim 1 wherein said photon detector is selected from the group consisting of: charge-coupled device ("CCD"), complementary metal oxide semiconductor ("CMOS") detector, and focal plane array sensor.

7. The system of claim 1 wherein said photon source is a laser.

8. The system of claim 1 wherein said second photons are selected from the group consisting of: fluorescence photons from said sample, photons emitted by said sample, photons reflected from said sample, and photons refracted by said sample.

9. The system of claim 1 wherein said second photons are scattered photons.

10. The system of claim 1 wherein said second photons are Raman scattered photons.

11. The system of claim 1 wherein a number of fibers in said predetermined group is one.

12. A system for detecting photons from a sample, comprising:

a photon source for illuminating a first portion of a sample with first photons to thereby produce second photons;

a fiber array spectral translator comprising plural fibers for receiving said second photons and directing said second photons to said photon detector, wherein only a first predetermined group of said plural fibers receive and direct said second photons to said photon detector, and wherein each fiber in said first predetermined group is associated with a predetermined different second portion of said sample wherein each of said predetermined different second portions is smaller than said first portion; and said photon detector for detecting said second photons.

13. The system of claim 12 wherein a number of fibers in said predetermined group is less than or equal to twenty-five percent of a total number of fibers in said fiber array spectral translator.

14. The system of claim 12 wherein a number of fibers in said predetermined group is less than or equal to ten percent of a total number of fibers in said fiber array spectral translator.

15. The system of claim 12 wherein a number of fibers in said predetermined group is less than or equal to one percent of a total number of fibers in said fiber array spectral translator.

16. The system of claim 12 wherein ones of said predetermined different second portions overlap.

17. The system of claim 12 wherein said photon detector is selected from the group consisting of: charge-coupled device ("CCD"), complementary metal oxide semiconductor ("CMOS") detector, and focal plane array sensor.

18. The system of claim 12 wherein said photon source is a laser.

19. The system of claim 12 wherein said second photons are selected from the group consisting of: fluorescence photons from said sample, photons emitted by said sample, photons reflected from said sample, and photons refracted by said sample.

20. The system of claim 12 wherein said second photons are scattered photons.

21. The system of claim 12 wherein said second photons are Raman scattered photons.

22. The system of claim 12 wherein a number of fibers in said predetermined group is one.

23. The system of claim 12 wherein said photon source illuminates said first portion of the sample with first photons via a second predetermined group of said plural fibers.

24. The system of claim 23 wherein said first and second predetermined groups are the same and said first and second portions of the sample are substantially the same.

25. The system of claim 23 wherein said first predetermined group is a first predetermined one of said plural fibers.

26. The system of claim 25 wherein said first portion is smaller than said second portion.

27. The system of claim 23 wherein said second predetermined group is a second predetermined one of said plural fibers.

28. The system of claim 27 wherein said second portion is smaller than said first portion.

29. The system of claim 23 wherein said first predetermined group is a first predetermined one of said plural fibers and wherein said second predetermined group is a second predetermined one of said plural fibers.

30. The system of claim 12 further comprising:
a display device, and
a microprocessor unit operatively connected to said photon detector and to said display device,
wherein said photon detector sends to said microprocessor a first signal representative of said second photons, and
wherein said microprocessor unit forms a second signal from said first signal and sends said second signal to said display device to display a first visual representation of said second signal.

31. The system of claim 30 wherein said first visual representation is a spectrum.

32. The system of claim 31 wherein said spectrum is a Raman spectrum.

33. The system of claim 30 wherein said first visual representation is an image.

34. The system of claim 33 wherein said image is a Raman image.

35. The system of claim 33 wherein said microprocessor unit runs a software program for forming said second signal from said first signal.

36. The system of claim 30 wherein said display device comprises a user-input screen for a user to select a portion of said first visual representation.

37. The system of claim 30 wherein said user-input screen is a touch-screen.

38. The system of claim 30 further comprising a user input device operatively connected to said microprocessor unit, wherein said input device enables a user to select a portion of said first visual representation.

39. The system of claim 38 wherein said user input device is a computer mouse.

40. The system of claim 30 wherein a memory stores a second visual representation, and wherein said microprocessor unit further comprises circuitry for overlaying said first visual representation on said second visual representation.

41. The system of claim 40 wherein said second visual representation is an optical image of said sample.

42. The system of claim 41 wherein said second visual representation is an optical image of a third portion of said sample.

43. The system of claim 42 wherein said third portion of said sample is substantially the same as said first portion of said sample.

44. The system of claim 12 wherein said first photons have a wavelength selected from the group of wavelengths consisting of: ultraviolet light, visible light, near infrared light, infrared light, and combinations thereof.

45. The system of claim 12 wherein said second photons are fluorescence emission photons from said sample.

46. A method for detecting photons from a sample, comprising:
illuminating a first portion of a sample with first photons to thereby produce second photons;
receiving said second photons using a fiber array spectral translator comprising plural fibers and directing said second photons to said photon detector using said fiber array spectral translator, wherein only a first predetermined group of said plural fibers receive and direct said second photons to said photon detector, and wherein each fiber in said first predetermined group is associated with a predetermined different second portion of said sample wherein each of said predetermined different second portions is smaller than said first portion; and
detecting said second photons using said photon detector.

47. The method of claim 46 wherein a number of fibers in said predetermined group is less than or equal to twenty-five percent of a total number of fibers in said fiber array spectral translator.

48. The method of claim 46 wherein a number of fibers in said predetermined group is less than or equal to ten percent of a total number of fibers in said fiber array spectral translator.

49. The method of claim 46 wherein a number of fibers in said predetermined group is less than or equal to one percent of a total number of fibers in said fiber array spectral translator.

50. The method of claim 46 wherein ones of said predetermined different second portions overlap.

51. The method of claim 46 wherein said photon detector is selected from the group consisting of: charge-coupled device ("CCD"), complementary metal oxide semiconductor ("CMOS") detector, and focal plane array sensor.

52. The method of claim 46 wherein said photon source is a laser.

53. The method of claim 46 wherein said second photons are selected from the group consisting of: fluorescence photons from said sample, photons emitted by said sample, photons reflected from said sample, and photons refracted by said sample.

54. The method of claim 46 wherein said second photons are scattered photons.

55. The method of claim 46 wherein said second photons are Raman scattered photons.

56. The method of claim 46 wherein a number of fibers in said predetermined group is one.

57. The method of claim 46 wherein said photon source illuminates said first portion of the sample with first photons via a second predetermined group of said plural fibers.

58. The method of claim 57 wherein said first and second predetermined groups are the same and said first and second portions of the sample are substantially the same.

59. The method of claim 57 wherein said first predetermined group is a first predetermined one of said plural fibers.

60. The method of claim 59 wherein said first portion is smaller than said second portion.

61. The method of claim 57 wherein said second predetermined group is a second predetermined one of said plural fibers.

62. The method of claim 61 wherein said second portion is smaller than said first portion.

63. The method of claim 57 wherein said first predetermined group is a first predetermined one of said plural fibers and wherein said second predetermined group is a second predetermined one of said plural fibers.

64. The method of claim 46 further comprising:
sending a first signal representative of said second photons to a microprocessor unit, wherein said microprocessor unit forms a second signal from said first signal;
sending said second signal from said microprocessor unit to a display device, and
displaying a first visual representation of said second signal.

65. The method of claim 64 wherein said first visual representation is a spectrum.

66. The method of claim 65 wherein said spectrum is a Raman spectrum.

67. The method of claim 64 wherein said first visual representation is an image.

68. The method of claim 67 wherein said image is a Raman image.

69. The method of claim 67 wherein said microprocessor unit runs a software program for forming said second signal from said first signal.

70. The method of claim 64 further comprising receiving input from a user on said display device comprising a user-input screen, wherein said user selects a portion of said first visual representation.

71. The method of claim 64 wherein said user-input screen is a touch-screen.

72. The method of claim 64 further comprising a receiving input from a user input device operatively connected to said microprocessor unit, wherein said user selects a portion of said first visual representation.

73. The method of claim 72 wherein said user input device is a computer mouse.

74. The method of claim 64 further comprising storing a second visual representation in a memory device, and overlaying said first visual representation on said second visual representation.

75. The method of claim 74 wherein said second visual representation is an optical image of said sample.

76. The method of claim 75 wherein said second visual representation is an optical image of a third portion of said sample.

77. The method of claim 76 wherein said third portion of said sample is substantially the same as said first portion of said sample.

78. The method of claim 46 wherein said first photons have a wavelength selected from the group of wavelengths consisting of: ultraviolet light, visible light, near infrared light, infrared light, and combinations thereof.

79. The method of claim 46 wherein said second photons are fluorescence emission photons from said sample.

* * * * *